(12) United States Patent
Brinkmann et al.

(10) Patent No.: US 12,295,655 B2
(45) Date of Patent: May 13, 2025

(54) BODILY SUBSTANCE DETECTION BY EVALUATING PHOTOLUMINESCENT RESPONSE TO EXCITATION RADIATION

(71) Applicant: Boston Scientific Corporation, Marlborough, MA (US)

(72) Inventors: Ralf Brinkmann, Grevenbroich (DE); Birgit Lange, Lübeck (DE)

(73) Assignee: Boston Scientific Corporation, Marlborough, MA (US)

( * ) Notice: Subject to any disclaimer, the term of this patent is extended or adjusted under 35 U.S.C. 154(b) by 0 days.

(21) Appl. No.: 18/197,479

(22) Filed: May 15, 2023

(65) Prior Publication Data
US 2023/0285079 A1    Sep. 14, 2023

Related U.S. Application Data

(63) Continuation of application No. 16/864,358, filed on May 1, 2020, now Pat. No. 11,672,600, which is a
(Continued)

(51) Int. Cl.
*A61B 18/26*    (2006.01)
*A61B 5/00*    (2006.01)
(Continued)

(52) U.S. Cl.
CPC ............ *A61B 18/26* (2013.01); *A61B 5/0071* (2013.01); *A61B 5/0075* (2013.01);
(Continued)

(58) Field of Classification Search
CPC .......... A61B 2018/00452; A61B 2018/00696; A61B 2018/00642; A61B 2018/00107;
(Continued)

(56) References Cited

U.S. PATENT DOCUMENTS 4,682,594 A    7/1987    Mok
4,718,417 A    1/1988    Kittrell et al.
(Continued)

FOREIGN PATENT DOCUMENTS

CN    102015020 A    4/2011
JP    5285159 B2    9/2013
(Continued)

OTHER PUBLICATIONS

International Search Report and Written Opinion of International Application No. PCT/US2016/036678, dated Oct. 26. (15 pages).
(Continued)

*Primary Examiner* — Brian T Gedeon
(74) *Attorney, Agent, or Firm* — Seager, Tufte & Wickhem, LLP

(57) ABSTRACT

A medical device may include an ablation device configured to deliver ablation energy to a treatment site. The medical device may further include a probe device configured to deliver excitation radiation to the treatment site. Further the medical device may include a radiation-receiving device configured to receive photoluminescence radiation emitted from the treatment site in response to the treatment site being illuminated by the excitation radiation and to generate a detection signal in response to the received photoluminescence radiation. Additionally, the excitation radiation may be different from the ablation energy.

14 Claims, 12 Drawing Sheets

Related U.S. Application Data continuation of application No. 15/177,888, filed on Jun. 9, 2016, now Pat. No. 10,709,505.

(60) Provisional application No. 62/173,840, filed on Jun. 10, 2015.

(51) Int. Cl.
| | | |
|---|---|---|
| *A61B 5/06* | (2006.01) | |
| *A61B 18/00* | (2006.01) | |
| *A61B 18/20* | (2006.01) | |
| *A61B 18/24* | (2006.01) | |
| *A61B 5/20* | (2006.01) | |
| *A61B 17/00* | (2006.01) | |

(52) U.S. Cl.
CPC .............. *A61B 5/0084* (2013.01); *A61B 5/06* (2013.01); *A61B 18/20* (2013.01); *A61B 18/24* (2013.01); *A61B 18/245* (2013.01); *A61B 5/20* (2013.01); *A61B 2017/00061* (2013.01); *A61B 2017/00066* (2013.01); *A61B 2018/00505* (2013.01); *A61B 2018/00577* (2013.01); *A61B 2018/00666* (2013.01); *A61B 2018/00773* (2013.01); *A61B 2018/00785* (2013.01); *A61B 2018/00904* (2013.01)

(58) Field of Classification Search
CPC .......... A61B 2018/00125; A61B 2018/00351; A61B 2018/00815; A61B 2018/00821
See application file for complete search history.

(56) References Cited

U.S. PATENT DOCUMENTS

| | | |
|---|---|---|
| 4,785,806 A | 11/1988 | Deckelbaum |
| 4,973,848 A | 11/1990 | Kolobanov et al. |
| 5,275,594 A | 1/1994 | Baker et al. |
| 5,350,375 A | 9/1994 | Deckelbaum et al. |
| 5,382,163 A | 1/1995 | Putnam |
| 5,842,995 A | 12/1998 | Mahadevan-Jansen et al. |
| 6,055,451 A | 4/2000 | Bambot et al. |
| 8,696,653 B2 | 4/2014 | Melsky et al. |
| 2001/0055462 A1 | 12/2001 | Seibel |
| 2003/0138378 A1 | 7/2003 | Hashimshony |
| 2006/0058683 A1 | 3/2006 | Chance |
| 2006/0190006 A1 | 8/2006 | Oka et al. |
| 2008/0200861 A1 | 8/2008 | Shalev et al. |
| 2008/0226029 A1 | 9/2008 | Weir et al. |
| 2008/0255461 A1 | 10/2008 | Weersink et al. |
| 2009/0156900 A1 | 6/2009 | Robertson |
| 2009/0281536 A1 | 11/2009 | Beckman et al. |
| 2011/0165534 A1 | 7/2011 | Berube-Lauziere et al. |
| 2012/0179030 A1 | 7/2012 | McGreevy et al. |

FOREIGN PATENT DOCUMENTS

| | | |
|---|---|---|
| JP | 6284776 B2 | 2/2018 |
| WO | 9005563 A1 | 5/1990 |
| WO | 2009032016 A1 | 3/2009 |
| WO | 2010021722 A1 | 2/2010 |
| WO | 2014011466 A1 | 1/2014 |
| WO | 2014097008 A1 | 6/2014 |

OTHER PUBLICATIONS

Muller et al., "Imaging Thermal Expansion and Retinal Tissue changes during Photocoagualation by High Speed OCT," Biomedical Optics Express, vol. 3, No. 5, pp. 1025-1046, May 1, 2012.

EPO Communication pursuant to Article 94(3) EPC from corresponding European Patent Application No. 16732109.0 dated Mar. 4, 2019 (4 pages).

Goldey et al. "Development of a Smart Holmium: YAG Laser Lithotriptor", Lasers in Surgery and Medicine, Wiley-Liss, new York, US, vol. 21, No. 1, Jan. 1, 1997, pp. 20-28. ISSN: 0196-8092.

BODILY SUBSTANCE DETECTION BY EVALUATING PHOTOLUMINESCENT RESPONSE TO EXCITATION RADIATION

CROSS-REFERENCE TO RELATED APPLICATION

This application is a continuation of U.S. application Ser. No. 16/864,358, filed May 1, 2020, which is a continuation of U.S. application Ser. No. 15/177,888, filed Jun. 9, 2016, which claims the benefit of priority from U.S. Provisional Application No. 62/173,840, filed Jun. 10, 2015, each of which is incorporated by reference herein in its entirety.

FIELD OF TECHNOLOGY

The present disclosure relates to devices and methods for detecting specific types of bodily substances in vivo. In particular, the present disclosure relates to detecting human stones in vivo by evaluating photoluminescence radiation, for example fluorescence radiation, emitted by human stones excited by a comparatively low-power probe device.

BACKGROUND

Human stones, e.g., urinary stones, can form in the human body, e.g., in the human urinary system from minerals in the urine. For the sake of conciseness, the subsequent discussion will focus on urinary stones. However, the below said is similar applicable to other human stones (e.g., bile stones, pancreatic stones, salivary stones or gall stones).

Urinary stones can cause painful and potentially harmful conditions. Therefore, removal of urinary stones can be indicated. For this purpose, there exist different techniques involving different medical devices. In some examples, a medical device (e.g., a ureteroscope) can be adapted to deliver ablation energy (e.g., ablation energy in the form of electromagnetic radiation) to the urinary stone. The ablation energy causes disintegration of the human stone (lithotripsy). The debris of the human stone can subsequently be removed or leave the human body through the urinary system.

The disintegration of human stones can require a substantial amount of ablation energy. In addition, the lithotripsy treatment is frequently involves an endoscopic procedure. During this procedure, a medical practitioner might not have clear sight of a treatment site including the urinary stone (for instance, a urinary stone located in a ureter) to be disintegrated. This limited visual access in combination with the involved high energies can lead to complications including damaging of tissue by applying ablative energy. For instance, applying ablative energy can perforate walls of the urinary system. In order to avoid such complications, techniques are required to detect whether a medical device for lithotripsy is located at or near a human stone or not.

SUMMARY

In one aspect, the present disclosure relates to a medical device comprising an ablation device configured to deliver ablation energy to a treatment site, a probe device configured to deliver excitation radiation to the treatment site and a radiation-receiving device configured to receive photoluminescence radiation, for example fluorescence radiation, emitted from the treatment site in response to being illuminated by the excitation radiation and to generate a detection signal in response to the received photoluminescence radiation, the excitation radiation being different from the ablation energy.

In some prior art lithotripsy systems, the ablation energy itself is used to excite a bodily substance at the treatment site and electromagnetic radiation generated in response to delivery of the ablation energy has been used to discriminate between human stones and other bodily substances (e.g., tissue). In some examples, a radiative response caused by a leading edge of laser pulses for ablation of human stones has been analyzed for human stone detection. In these systems, if the radiative response indicates that the bodily substance to be ablated is not a human stone, the delivery of the ablation energy is interrupted (e.g., by a fast switch). This technique, however, requires that the same laser source (e.g., the same wavelength range) is used for ablation and for human stone detection. As a result, the required energies to elicit an adequate response can be high. For some lasers or laser operation parameters which are useful for human stone ablation, no adequate photoluminescence response might be obtainable at all. The techniques of the present disclosure can address these issues.

Using excitation radiation other than the ablation energy for exciting a photoluminescence response that can be processed to determine a type of bodily substance onto which the excitation signal (and potentially the ablation energy) is applied can have one or more advantages.

In one example, a medical device may include an ablation energy source, an excitation radiation source, and a radiation receiving device including a phase-sensitive detection device having a lock-in amplifier. The medical device may further include a probe operably coupled to the ablation energy source, the excitation radiation source, and the radiation receiving device. Further, the medical device may include a pulse generator operably coupled to the excitation radiation source.

The medical device may include any one or more of the following features. The radiation receiving device may be at least one of a photodiode and a photo resister. The phase-sensitive detection device may include a lock-in amplifier. The device may further include a plurality of dichroic mirrors. The probe may include an optical fiber.

In a further example, a medical device may include a first laser energy source and a second laser energy source. The medical device may also include a radiation receiving device including a lock-in amplifier. Further, the medical device may include a probe operably coupled to the first laser energy source, the second laser energy source, and the radiation receiving device.

The medical device may include any one or more of the following features. The radiation receiving device may be at least one of a photodiode and a photo resister. The medical device may further include a pulse generator operably coupled to the second laser energy source. The medical device may further include a first mirror operably positioned between an emission path of the first laser energy source and the probe; and a second mirror operably positioned between an emission path of the second laser energy source and the probe. The first mirror may be transmissive of energy having a wavelength in the invisible light spectrum and reflective of energy having a wavelength in the visible light spectrum. The second mirror may be reflective of energy having a wavelength in the visible light spectrum, and transmissive of photoluminescence radiation.

In a further example, a method may include delivering excitation radiation having a wavelength in the visible spectrum of light to a treatment site and receiving radiation from the treatment site in response to the excitation radiation. The method also may include discriminating a target from a remainder of the treatment site based on the received radiation and damaging the target via an ablation energy. Further, the method may include continuing delivery of the excitation radiation during the damaging step.

Examples of the method may further include any one or more of the following features. The wavelength of the excitation radiation may be about 532 nm. The ablation energy may be pulsed. The received radiation from the treatment site may be photoluminescence radiation. Delivering ablation energy may further include delivering ablation energy via a mechanical lithotripsy device. Delivering ablation energy may further include delivering radiation having a wavelength in the invisible spectrum of light. Discriminating a target from a remainder of the treatment site based on the received radiation may include comparing an intensity of the received radiation to a predetermined threshold intensity. The method may further include stopping damaging the target via the ablation energy when the intensity of the received radiation is below the predetermined threshold intensity. Damaging the target via the ablation energy may be done in response to the received radiation from the treatment site in response to the excitation radiation.

Firstly, a source of excitation energy can be freely selected in view of eliciting an appropriate (e.g., maximal) photoluminescence response. This can allow using a detection technique based on a photoluminescence signal irrespective of the ablation device employed (e.g., irrespective of a wavelength of an ablation laser). In some cases, the wavelength of a laser source used for ablation can be ill-suited for generating a photoluminescence response (e.g., a laser source emitting in the mid-infrared wavelength range). For instance, Ho:YAG lasers frequently used in lithotripsy procedures. In the devices of the present disclosure, an excitation wavelength of the probe device can be selected independently of a wavelength of an ablation energy source.

Secondly, an ablation device can be configured in a comparatively simple manner. For instance, no means for shutting down a pulsed ablation energy source after a predetermined time is required in some examples of the present disclosure, as the excitation radiation can be applied and controlled independently of the ablation energy.

Thirdly (and as a consequence), a comparatively low energy can be used to determine a type of bodily substance in an ablation region of an ablation device. As a result, when using the techniques of the present disclosure a risk of damaging tissue by the probe device can be reduced. For instance, an energy level of the employed excitation radiation can be below a maximum permissible radiation for irradiating human skin (e.g., as set out in DIN EN 60825-1:2012-11). In some examples, the probe device might be permanently active while a medical practitioner operates the medical device.

Fourthly, the probe device's function can be provided by components of the ablation system already present in certain ablation system. For instance, a pilot laser for aiding a medical practitioner in navigating an endoscope can be used as source of the excitation radiation. Thus, the devices of the present disclosure do not have to have a considerably increased complexity compared to devices in which the ablation energy also serves as excitation radiation.

In a second aspect according to the first aspect the probe device includes one or more lasers.

In a third aspect according to the first aspect the probe device includes one or more light emitting diodes.

In a fourth aspect according to any one of the first to third aspects the probe device is configured to deliver excitation radiation in a pulsed manner.

In a fifth aspect according to any one of the first to fourth aspects the probe device is configured to deliver excitation radiation at the treatment site at energy levels adapted not to damage tissue at the treatment site.

In a sixth aspect according to any one of the first to fifth aspects the probe device is configured to deliver the excitation radiation at the treatment site at an energy level that does not exceed a maximum permissible radiation for irradiating human skin as set out in DIN EN 60825-1:2012-11.

In a seventh aspect according to any one of the first to sixth aspects the probe device is configured to deliver is configured to deliver the excitation radiation at the treatment site at below 20 mJ per second, preferably below 5 mJ per second, more preferably below 1 mJ per second.

In an eighth aspect according to any one of the first to seventh aspects the probe device is configured to deliver excitation energy at a wavelength in the range between 380 and 900 nm.

In a ninth aspect according to the eighth aspect the probe device is configured to deliver excitation energy at a wavelength in the range between 480 and 620 nm.

In a tenth aspect according to the ninth aspect the probe device is configured to deliver excitation energy at a wavelength in the range between 500 and 550 nm.

In an eleventh aspect according to any one of the first to tenth aspects the ablation device includes a laser as ablation energy source.

In a tenth aspect according to any one of the first to ninth aspects the ablation device includes an electrohydraulic probe.

In an eleventh aspect according to the tenth aspect the laser is a solid-state laser.

In a twelfth aspect according to the eleventh aspect the laser has a wavelength in the range between 1.4 µm and 3 µm.

In a thirteenth aspect according to the eleventh or twelfth aspect the laser is a YAG-based laser, preferably a Ho:YAG (having a wavelength of about 2.1 µm), a Tm:YAG laser (having a wavelength of about 2.1 µm) or an Er:YAG laser (having a wavelength of about 2.94 µm).

In a fourteenth aspect according to any one of the tenth to thirteenth aspects the laser delivers ablation energy at a pulse length between 100 us and 10 ms µs, a wavelength between 1600 nm and 2500 nm and a pulse energy between 50 mJ and 6 J.

In a fifteenth aspect according to any one of the preceding aspects the radiation-receiving device includes a waveguide and a detector, the waveguide being configured to at least partially guide the received photoluminescence radiation from the illuminated treatment site to the detector.

In a sixteenth aspect according to the fifteenth aspect waveguide includes one or more optical fibers.

In a seventeenth aspect according to the fifteenth or sixteenth aspect the waveguide is further configured to guide the ablation energy to the treatment site.

In an eighteenth aspect according to any one of the fifteenth to seventeenth aspects the waveguide is further configured to guide the excitation radiation to the treatment site.

In a nineteenth aspect according to any one of the preceding aspects the probe device includes a modulator to modulate an intensity of the excitation radiation.

In a twentieth aspect according to any one of the preceding aspects the radiation-receiving device includes a device for phase sensitive detection of the received photoluminescence radiation.

In a twenty-first aspect according to the twentieth aspect the device for phase sensitive detection is a lock-in amplifier.

In a twenty-second aspect according to any one of the preceding aspects generating the detection signal includes using one or more reference measurements during which the excitation radiation is not delivered to the treatment site.

In a twenty-third aspect according to any one of the preceding aspects the medical device further includes a controller configured to determine one or more parameters based on the received photoluminescence radiation and wherein the medical device is configured to generate an output signal indicative of a type of bodily substance present at the treatment site based on the one or more parameters.

In a twenty-fourth aspect according to the twenty-third aspect determining the one or more parameters includes determining that an intensity of the received photoluminescence radiation exceeds a predetermined threshold.

In a twenty-fifth aspect according to the twenty-third or twenty-fourth aspect determining the one or more parameters includes determining a level of intensity of the received photoluminescence radiation.

In a twenty-sixth aspect according to the twenty-third, twenty-fourth or twenty-fifth aspects determining the one or more parameters includes determining an intensity of the received photoluminescence radiation in one or more predetermined wavelength ranges.

In a twenty-seventh aspect according to any one of the twenty-third to twenty-sixth aspects determining the one or more parameters includes evaluating a spectrum of the received photoluminescence radiation.

In a twenty-eighth aspect according to any one of the twenty-third to twenty-seventh aspects the output signal indicates that the treatment site comprises a particular type of bodily substance.

In a twenty-ninth aspect according to any one of the twenty-second to twenty-sixth aspects the output signal indicates that the treatment site comprises a particular type of human stone.

In a thirtieth aspect according to the twenty-ninth aspect the output signal indicates that the treatment site includes at least a portion of a human stone.

In a thirty-first aspect according to any one of the twenty-third to thirtieth aspects controller is configured to determine a distance between a bodily object and the medical device based on the one or more parameters.

In a thirty-second aspect according to the thirty-first aspect the bodily object is a human stone.

In a thirty-third aspect according to any one of the preceding aspects the excitation radiation includes two or more separate wavelengths.

In a thirty-fourth aspect according to any one of the preceding aspects the excitation radiation and the ablation energy are generated by two different sources included in the medical device.

In a thirty-fifth aspect according to any one of the preceding aspects the excitation radiation is generated by a pilot laser of the medical device.

In a thirty-sixth aspect according to any one of the preceding aspects the medical device is a lithotripsy device.

In a thirty-seventh aspect according to any one of the preceding aspects the medical device is a device to remove soft or hard tissue.

In a thirty-eighth aspect according to any one of the preceding aspects the medical device is configured to deliver ablation energy and the excitation radiation through an endoscopic access.

In a thirty-ninth aspect according to the thirty-fifth aspect the medical device includes an ureteroscope or a pyeloscope In a fortieth aspect according to any one of the preceding aspects the medical device is configured to deliver ablation energy and the excitation radiation through a catheter.

In a forty-first aspect according to any one of the preceding aspects the photoluminescence radiation includes radiation in a wavelength range between 500 nm and 800 nm.

In a forty-second aspect a method of detecting a human stone in vivo comprises receiving photoluminescence radiation emitted from a treatment site in response to being illuminated by excitation radiation and detecting a human stone in the treatment site based on the received photoluminescence radiation, wherein the excitation radiation at the treatment site has an energy level adapted not to damage tissue at the treatment site.

In a forty-third aspect a method of detecting a human stone in vivo, the method comprising delivering excitation radiation to a treatment site, receiving photoluminescence radiation emitted from the treatment site in response to being illuminated by the excitation radiation and detecting a human stone in the treatment site based on the received photoluminescence radiation, wherein the excitation radiation at the treatment site has an energy level adapted not to damage tissue at the treatment site.

In a forty-fourth aspect a method of detecting a human stone in vivo comprises receiving photoluminescence radiation emitted from a treatment site in response to being illuminated by excitation radiation and detecting a human stone in the treatment site based on the received photoluminescence radiation, wherein the excitation radiation at the treatment site is delivered at below 20 mJ per second, preferably below 5 mJ per second, more preferably below 1 mJ per second.

In a forty-fifth aspect a method of detecting a human stone in vivo comprises receiving photoluminescence radiation emitted from a treatment site in response to being illuminated by excitation radiation and detecting a human stone in the treatment site based on the received photoluminescence radiation, wherein the excitation radiation delivered at the treatment site delivered does not exceed a maximum permissible radiation for irradiating human skin as set out in DIN EN 60825-1:2012-11.

In a forty-sixth aspect according to the forty-second or the forty-fifth aspect, the method further comprising generating an output signal indicative of whether the treatment site includes a human stone or not.

In a forty-seventh aspect according to the forty-sixth aspect the method further determining one or more parameters of the received photoluminescence radiation to detect the human stone in the treatment site.

In a forty-eighth aspect according to the forty-sixth aspect determining the one or more parameters includes one or determining that an intensity of the received photoluminescence radiation exceeds a predetermined threshold.

In a forty-ninth aspect according to the forty-seventh or the forty-eighth aspect wherein determining the one or more parameters includes determining a level of intensity of the received photoluminescence radiation.

In a fiftieth aspect according to any one of the forty-seventh to forty-ninth aspects determining the one or more parameters includes determining an intensity of the received photoluminescence radiation in one or more predetermined wavelength ranges.

In a fifty-first aspect according to any one of the forty-seventh to fiftieth aspects determining the one or more parameters includes evaluating a spectrum of the received photoluminescence radiation.

In a fifty-second aspect according to any one of the forty-second to fifty-first aspects detecting a human stone in the treatment site includes determining a distance between a medical device for delivering the excitation energy and the human stone based on the received photoluminescence radiation.

In a fifty-third aspect according to any one of the forty-second to fifty-second aspects detecting a human stone includes a phase sensitive detection of the photoluminescence radiation.

In a fifty-fourth aspect according to any one of the forty-second to fifty-third aspects the method further includes inhibiting a delivery of ablation energy if no human stone is detected in the treatment site.

In a fifty-fifth aspect according to any one of the forty-second to fifty-second fourth the method further includes delivering ablation energy to the human stone if a human stone is detected in the treatment site.

In a fifty-sixth aspect according to any one of the forty-second to fifty-fifth aspects the method further includes one or more parameters of the delivery of the ablation energy are adjusted based on one or more parameters of the detected photoluminescence radiation.

In a fifty-seventh aspect according to any one of the forty-second to fifty-sixth aspects the excitation radiation is generated by a pilot laser of an endoscope.

In a fifty-eighth aspect an endoscope comprises an ablation laser configured to deliver ablation energy to a treatment site, a probe laser configured to deliver excitation radiation to the treatment site, a phase-sensitive receiver device configured to receive photoluminescence radiation emitted from the treatment site in response to being illuminated by the excitation radiation and a controller configured to detect a human stone in the treatment site based on the received photoluminescence radiation.

In a fifty-ninth aspect according to the fifty-eighth aspect the excitation radiation is delivered at below 50 mJ/s. preferably below 20 mJ/s, more preferably below 5 mJ/s.

In a sixtieth aspect according to one of the first to forty-first aspects the delivery of the ablation energy is triggered in response to the detection signal.

In a sixty-first aspect according to one of the first to forty-first aspects the delivery of the ablation energy is suppressed in response to the detection signal.

In a sixty-second aspect according to one of the first to forty-first aspects one or more operation parameters of the ablation device are adjusted in response to the detection signal.

In a sixty-third aspect according to one of the first to forty-first aspects the excitation radiation and the ablation energy are not delivered to the treatment site at the same time.

SHORT DESCRIPTION OF THE FIGURES

DETAILED DESCRIPTION

In connection with FIG. 1, an example medical device for ablating a bodily substance according to the present invention will be discussed. Subsequently, a particular system for detecting human stones will be discussed in connection with FIGS. 2 and 3. Experimental data showing signals of different human stones measured ex-vivo will be discussed in connection with FIGS. 4 to 11. Lastly, particular details of human stone detection based on a photoluminescence signal will be discussed in connection with FIG. 12.

General Aspects of an Ablation Device

Figure 1:
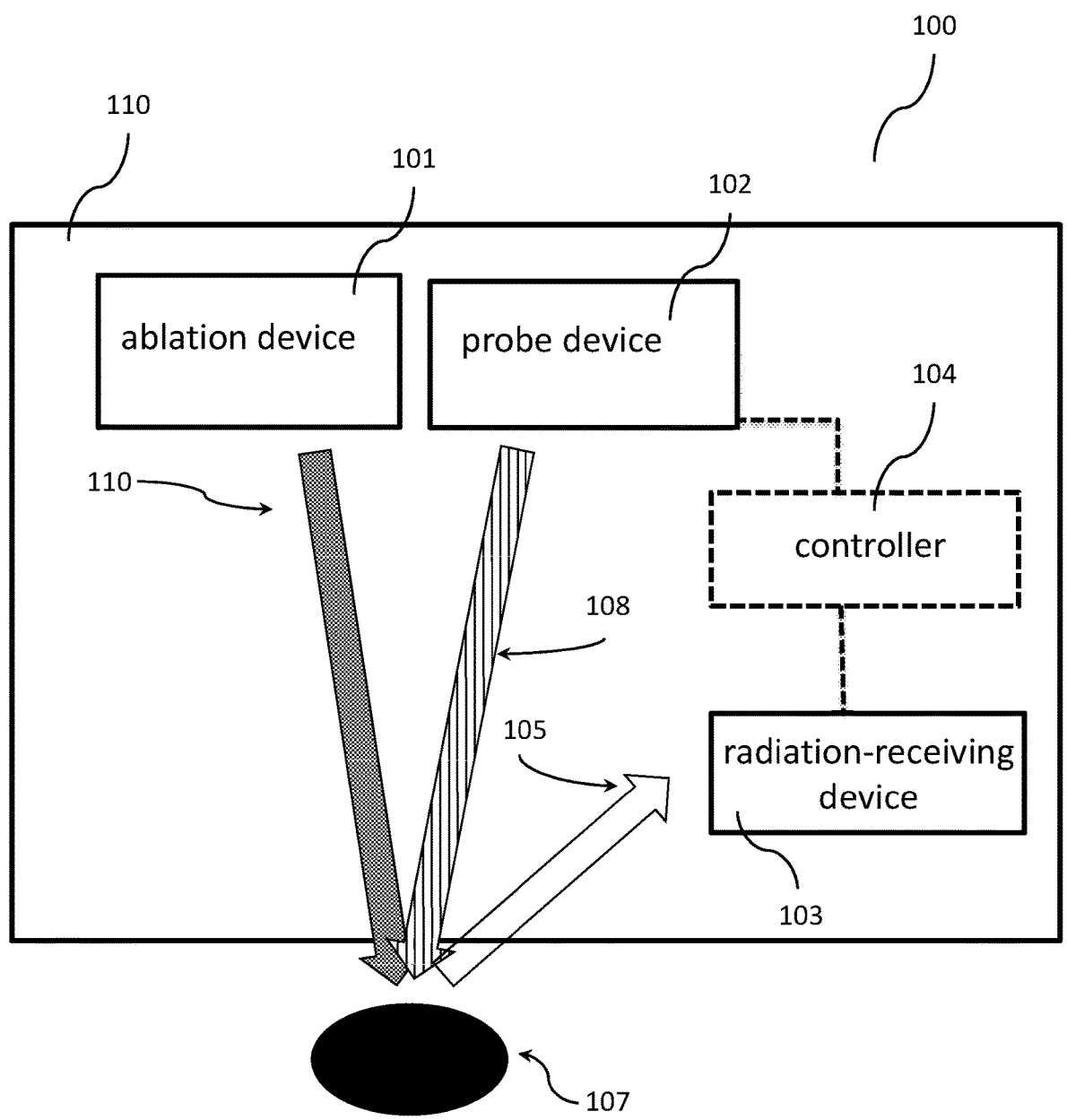
FIG. 1 shows an example medical device for ablating a bodily substance according to the present disclosure.

FIG. 1 shows a schematic drawing of a medical device 110 for ablating a bodily substance. In the present disclosure, the term "bodily substance," includes soft and hard tissue as well as non-cellular bodily substances (e.g., human stones and calcifications).

The medical device 110 includes an ablation device 101 configured to deliver ablation energy 110 to a treatment site 107, a probe device 102 configured to deliver excitation radiation 108 to the treatment site 107 and a radiation-receiving device 103 configured to receive photoluminescence radiation 105 (for example, fluorescence radiation) emitted from the treatment site 107 in response to being illuminated by the excitation radiation 108 and configured to output a detection signal in response to the received photoluminescence radiation 105. As can be seen in FIG. 1 the excitation radiation 108 is different from (and can be applied at a different time than) the ablation energy 110. For instance, the excitation radiation can be generated by a different source than the ablation energy. In other examples, one or more parameters of a source of ablation energy can be changed to generate the excitation radiation (e.g., a wavelength of a laser source). In any case, the excitation radiation is not provided as a treatment beam (e.g., as part of a pulse used for human stone ablation).

In the present disclosure the term "treatment site" is not limited to a site where actually ablation treatment takes place. Rather, this term is to be understood more generally as an area where treatment potentially takes place (e.g., an operation area of an ablation device).

The medical device 110 also includes an optional controller 104 for processing the detection signal and/or controlling one or more of the probe device and the radiation-receiving device.

The elements of the medical device 110 will be discussed in more detail in the following.

The ablation device 101 can be any device suitable for ablation of a particular type of bodily substance. The tissue to be ablated can include one or more of soft tissue, hard tissue or non-cellular bodily substances (e.g., human stones). Different example bodily substances that can be ablated are discussed below. In one example, the bodily substance to be ablated is a human stone in a human urinary system or a bile duct. However, even though the following discussion mainly focuses on ablating human stones, the techniques of the present disclosure are not limited to human stone ablation. The devices and methods of the present disclosure can also be applied for other treatments. For instance, ablation energy can be applied to ablate bodily substances in blood vessels, benign and malign tumor tissue, hemorrhoids, polyps, fibroids, calcifications, and any other bodily substances that are desired to be removed from a body. In general, the techniques described herein can be applied in any catheter-based or endoscopic medical device including an ablation device to ablate bodily substances.

Moreover, even though the present description focuses on devices to treat human patients, the devices and techniques of the present disclosure can also be adapted to treat animals (and in particular non-human mammals).

In one example, the ablation device 101 can include a laser source to emit laser radiation. Subsequently, laser radiation will be discussed predominantly as ablation energy. However, the techniques of the present disclosure are not limited to medical devices employing laser ablation techniques. In general, the probe devices of the present disclosure can be used in combination with any suitable ablation device. For example, the ablation device can apply ablation energy in the form of electromagnetic radiation other than laser radiation, heat, cryogenic energy, high-frequency (HF) energy, acoustic energy (e.g., ultrasound energy) or in the form of a chemically active agent. For instance, the ablation device includes an electrohydraulic probe. In one example, the ablation device 101 is configured to apply ablation energy to destroy a human stone.

Besides a source to generate ablation energy (e.g., a laser source to emit laser energy), the ablation device can in some examples include guiding components to guide ablation energy to the treatment site. In one example, the guiding means include one or more waveguides to guide radiative ablation energy (e.g., laser energy) to the treatment site (as the ablation energy source is frequently remote from a treatment site). In one example, the one or more waveguides include one or more fiber-optic components.

In addition to the ablation device 101, the medical device 100 of FIG. 1 includes a probe device 102. The probe device 102 is configured to deliver excitation radiation 108 to the treatment site 107. In one example, the probe device 102 includes one or more laser sources to emit the excitation radiation 108 (e.g., a pilot laser of a medical device for ablating a bodily substance). In another example, the probe device 102 includes one or more light emitting diodes. In still other examples, the probe device includes a plasma radiation source (e.g., a gas discharge source).

The term "light" as used in the present specification is not restricted to the visible part of the electromagnetic spectrum (e.g., radiation having a wavelength between 380 nm and 780 nm). Rather, the term "light" also covers electromagnetic radiation in the ultraviolet and infrared wavelength ranges. In one example, the term "light" covers a wavelength between 100 nm and 20 µm.

A wavelength of the excitation radiation can be selected to be suitable for a particular type of bodily substance to be detected. In one example, the probe device is configured to deliver excitation energy at a wavelength in the range between 380 and 900 nm, preferably in the range between 480 and 620 nm and most preferably the range between 500 and 550 nm. As will be discussed in connection with FIGS. 3 and 4, in one example, a wavelength in the range between 500 and 550 nm (e.g., 532 nm) can be used to generate a sufficiently large photoluminescence signal in human stones.

The excitation radiation can include radiation at multiple wavelength. For instance, the excitation radiation can include two or more distinct wavelength bands.

The excitation radiation can have a narrow bandwidth (e.g., lower than 5 nm bandwidth) or a broad bandwidth (e.g., higher than 5 nm bandwidth).

In some examples the probe device is configured to emit the excitation radiation in a pulsed manner. The probe device can be configured to emit the pulsed excitation radiation at a frequency of between 100 Hz and 10 kHz. A pulse duration at these frequencies can be between 100 ps and 100 ms. In other examples, the probe device can generate the excitation radiation in a substantially continuous wave manner.

The probe device 102 can also include one or more waveguides to guide the excitation radiation towards the treatment site 107. In one example, the one or more waveguides can also be used to guide ablation energy in the form of electromagnetic radiation towards the treatment site (at least along a portion of the distance between the ablation energy source and the treatment site 107). In this case, the one or more waveguides form part of the ablation device and the probe device.

In general, the ablation device, the probe device and the radiation-receiving device include the respective sources and receivers as well as (if applicable) components to guide the energy or radiation to and from a target treatment site. This can mean that particular components, e.g., a waveguide, form part of two or more of these devices. In addition, the ablation device, the probe device and the radiation-receiving device not necessarily are "stand-alone" components. Rather, these components can be integrated into other components of a medical ablation device (e.g., into a pilot laser of a medical ablation device).

Besides the probe device 102 and the ablation device 101, the medical device 110 includes the radiation-receiving device 103 for receiving photoluminescence radiation 105 emitted from the treatment site 107 in response to being illuminated by the excitation radiation 108. In addition, the radiation-receiving device 103 is configured to output a detection signal in response to the received photoluminescence radiation 105.

The optional controller 104 can be configured to process the output detection signal to determine one or more parameters based on the received photoluminescence radiation. Moreover, the medical device 101 can be configured to generate an output signal indicative of a type of bodily substance of the treatment site based on the one or more parameters, may be configured to generate a signal that prevents emission of the ablation energy 110 based on the received photoluminescence radiation, or may be configured to generate a signal that causes ablation energy 110 to be emitted from ablation device 101, based on the received photoluminescence radiation. These techniques will be discussed in more detail below in connection with FIG. 12.

The radiation-receiving device 103 (optionally in cooperation with the controller 104) can generate the detection signal by employing a device for phase sensitive detection of the received photoluminescence radiation.

In one example, the probe device 102 can includes a modulator to modulate an intensity and of the excitation radiation (in particular if a phase-sensitive detection is used). For example, the probe device can be turned off and on periodically. In other examples, an intensity of the excitation radiation can be changed periodically.

In other examples, the probe device is configured to emit modulated excitation radiation by emitting the excitation radiation in a periodically pulsed manner. For instance, the probe device can be configured to emit the pulsed excitation radiation at a frequency of between 100 Hz and 10 kHz. A pulse duration at these frequencies can be between 100 ps and 100 ms.

In this manner, the received photoluminescence radiation is also (at least partially) modulated. The device for phase sensitive detection of the radiation-receiving device 103 can be configured to detect this modulated portion of the received photoluminescence radiation. In one example, the device for phase sensitive detection is a lock-in amplifier.

By using a phase-sensitive detection technique a signal-to-noise ratio of the detection process can be improved. As a consequence, a usable signal can be detected at a smaller excitation power than when not employing a phase sensitive detection. For example, an excitation energy of 20 mJ per second or lower (or 5 mJ per second peak or lower) can be sufficient to discriminate human stones from other bodily substances (e.g., soft tissue) in some example devices. In other examples, the probe device is configured to deliver the excitation radiation at a power that does not exceed a maximum permissible radiation for irradiating human skin as set out in DIN EN 60825-1:2012-11 (or any other suitable regulation for maximal allowable irradiation on human skin).

The radiation-receiving device 103 can include any suitable optical detector to detect photoluminescence radiation emitted from the treatment site to be ablated. For instance, a radiation-receiving device 103 can include a photodiode (e.g., an APD or a PIN photodiode). In other examples, the radiation-receiving device 103 can include a photo resistor. Moreover, the radiation-receiving device 103 can include two or more optical detectors. Furthermore, the radiation-receiving device 103 can include a spectrometer for detecting the received photoluminescence radiation emitted from the treatment site in a spectrally resolved manner.

The excitation radiation 108 and the ablation energy 106 not necessarily are perfectly aligned. In other words, the ablation energy can be applied to a slightly different volume of the body (e.g., smaller or larger) than the excitation radiation at the treatment site. Nevertheless, the areas in which the excitation radiation 108 and the ablation energy 106 have an overlap.

In FIG. 1 the ablation device 101 and the probe device 102 are drawn as separate devices. However, in the medical devices of the present disclosure the ablation device 101 and the probe device 102 not necessarily have to be separate devices. It is merely required that the generated excitation radiation be different from the ablation energy. For example, if the ablation energy is delivered in the form of electromagnetic radiation, the excitation energy can have a different wavelength than the ablation radiation.

In some examples, the ablation device 101 and the probe device 102 can share a predetermined number of components. For example, the ablation device can include a laser source for generating the ablation energy. This laser source can include a pump laser generating laser radiation at a different wavelength than a wavelength of the ablation radiation. Laser radiation of the pump laser can be used as excitation radiation. In other examples, the ablation device and the probe device can be integrated in one device whose wavelength can be adjusted. In this example, the ablation energy can be delivered at a first wavelength and the excitation radiation can be delivered at a second, different wavelength. In the present disclosure, the expression "at a wavelength" not necessarily means (only) a single wavelength. Rather, the expression "at a wavelength" also includes pulsed radiation or broadband radiation (such as the radiation emission of a light emitting diode). For instance, the expression "at a wavelength" can identify a center wavelength in these situations.

Example Endoscopic Devices

After having discussed the medical device for ablating bodily substances in general in connection with FIG. 1, a particular example of an endoscopic medical device for ablating bodily substances will subsequently be discussed in connection with FIGS. 2 and 3.

As already explained, the devices and methods of the present disclosure can be employed in lithotripsy treatments. The techniques of the present disclosure will be discussed in connection with a treatment of a human stone in the urinary tract subsequently. However, as already discussed, the techniques of the present disclosure (and in particular the devices discussed in connection with FIG. 2 and FIG. 3) are not limited to this type of treatment. For instance, the techniques can equally be applied in device to treat human stones in the bile duct or another bodily part.

Figure 2:
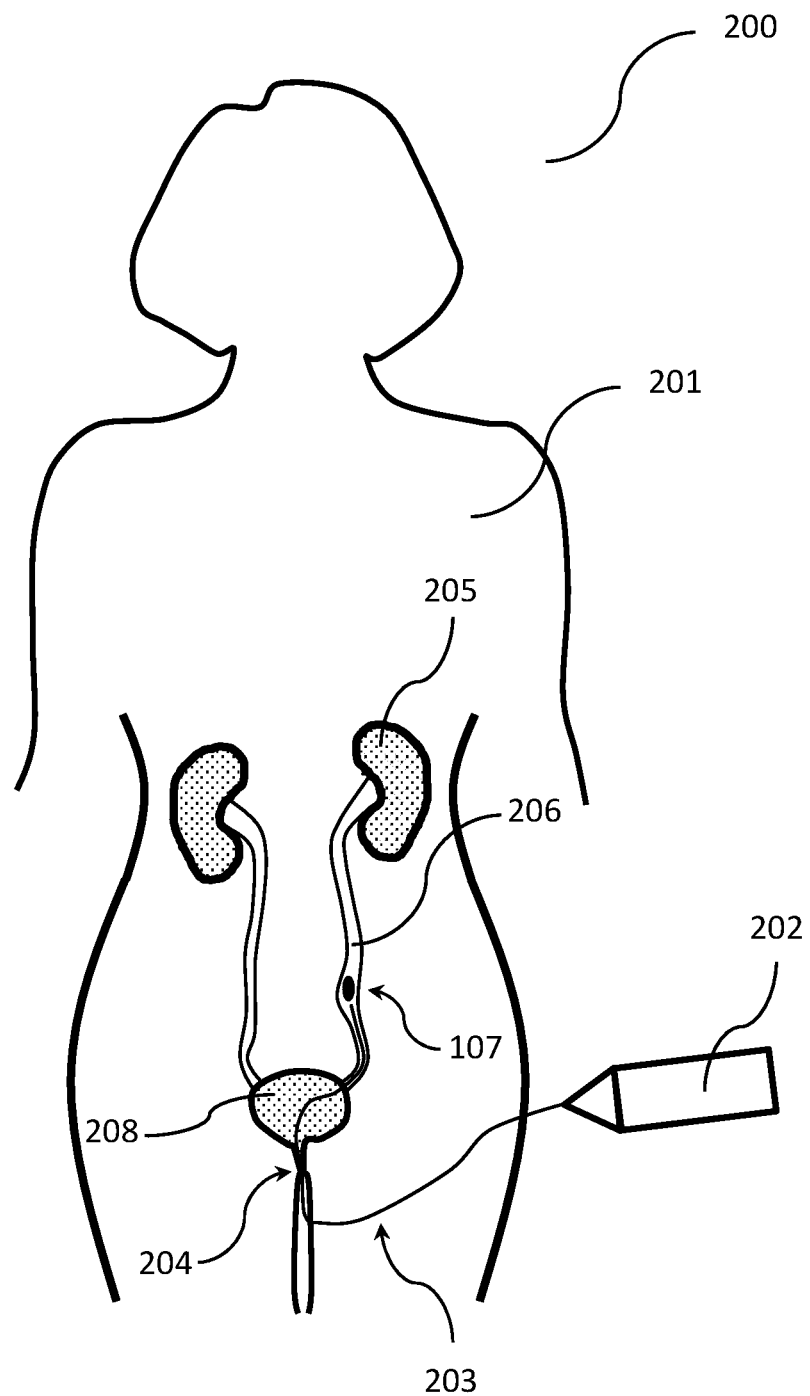
FIG. 2 depicts a schematic drawing of the human urinary system and an example medical device for ablating a bodily substance.

FIG. 2 shows a schematic drawing of the urinary system of a patient 201. Usually, the urinary system (or urinary tract) consist of two kidneys 205, two corresponding ureters 206, the bladder 208, and the urethra 204. FIG. 2 depicts a female patients having the above listed bodily parts. However, these parts equally are present in male patients. Human stones can be present in any of these bodily parts. Many human stones which cause issues and have to be removed are located in the ureters 206, as depicted in FIG. 2. In this example, a human stone 207 became stuck in the left ureter of the patient.

In the example of FIG. 2, the human stone 107 is to be disintegrated by a medical device 202. The medical device 202 of FIG. 2 can be an endoscope, where "endoscope" can comprise any suitable device for passing or directing the probe device or ablation device to a treatment site, including an endoscope, colonoscope, duodenoscope, cystoscope, hysteroscope, ureteroscope, pyeloscope, a pancreaticoscope or a endoscopic retrograde cholangiopancreatogram scope. A ureteroscope, for example, is a device that is capable of being passed through the urethra 204, the bladder 208 into one of the ureters 206, and up to the renal pelvis.

The endoscopes to be used for human stone destruction can include a flexible or rigid shaft 203, and one or multiple waveguides (e.g., a fiber-optic device) for delivering one or more of ablation energy, excitation radiation and photoluminescence radiation delivered to and emitted from a bodily substance present at the treatment site (e.g., a human stone).

In some examples, the medical devices for ablation of bodily substances discussed in connection with FIG. 1 can be integrated in an endoscope 202 (e.g., an ureteroscope or a pyeloscope). In these examples, the endoscope is configured to deliver the excitation radiation and the ablation energy from a position at the tip of the shaft (e.g., from a position which is less than 5 cm from the tip of the shaft). For instance, the ablation energy and the excitation radiation can be delivered through one or more waveguides. In addition, the photoluminescence radiation emitted by the treatment site can be delivered back to through the one or more waveguides through the shaft 203 to the radiation-receiving device of the medical device. In this example, the ablation energy source and the radiation source (e.g., an ablation laser and a probe laser) can be attached to the endoscope at a proximal position (e.g., at a port at a handle of the endoscope). For instance, an ablation laser and a laser of the probe device can be coupled to a waveguide of the endoscope through a fiber-optic coupler. In a similar manner, the photoluminescence radiation detecting device can be coupled to the endoscope at a proximal position (e.g., at a port at a handle of the endoscope).

In other examples, one or more of the ablation energy source, the radiation energy source and the radiation-receiving device can be integrated into the shaft or the handle of an endoscope.

In the example of FIG. 2, treatment of a human stone in the ureter (i.e., a kidney stone) has been discussed. In another example, the devices and methods of the present disclosure can be employed in medical devices for ablating bile, pancreatic, or gall stones. For instance, the medical devices for ablating bodily substances of the present disclosure can include an endoscope configured to be inserted in a bile duct for ablating bile stones. The endoscope can be configured to deliver ablation energy (e.g., laser energy) for bile stone ablation and an excitation radiation of a probe device used to detect a bile stone (discriminate a bile stone from other bodily substances, e.g., soft tissue).

In still other examples, the medical devices for ablating bodily substances of the present disclosure can be configured for insertion into other body cavities or vessels for ablating tissue.

Figure 3:
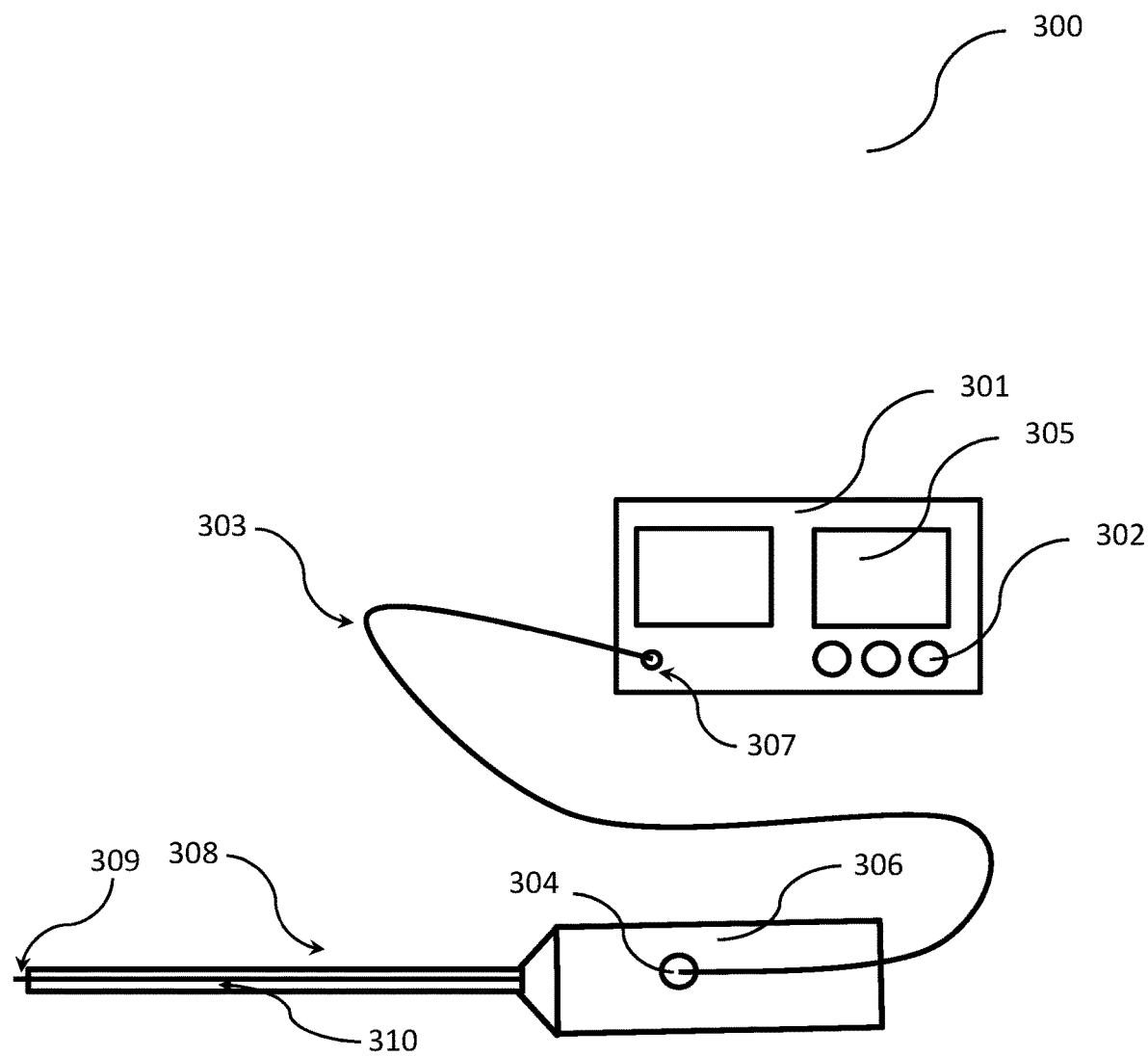
FIG. 3 depicts an example ureteroscope according to the present disclosure.

FIG. 3 shows an example of an endoscope for treating human stones including a medical device for ablation of bodily substances as discussed in connection with FIG. 1. This example device will be subsequently be discussed.

The example endoscope of FIG. 3 includes a medical device for ablating bodily substances with an ablation laser (or any other ablation energy source), a pilot laser (or any other excitation radiation source for generating excitation radiation) and a radiation-receiving device. In the example of FIG. 3 the ablation laser, the pilot laser and the radiation-receiving device (not shown in FIG. 3) are integrated in a single unit 301 (e.g., in a single housing). The unit 301 includes optical components to provide laser radiation of the ablation laser source and the excitation source to a port 307 of the console 301. In other examples, the unit 301 can include different ports for the ablation energy, the excitation radiation and/or the emitted photoluminescence radiation.

In addition, the exemplary unit 301 includes user input elements 302 which can allow a user to set one or more parameters of the medical device. Such parameters may allow the user to adjust the photoluminescence signal detection sensitivity or associated processing (e.g., adjust thresholds) used to determine a type of bodily substance onto which the excitation signal is applied (e.g., in connection with any of steps 502 through 505 described in connection with FIG. 5). Such user input elements 302 may likewise allow the user to set or adjust one or more parameters of the ablation device. Furthermore, the unit 301 can include one or more display elements 305 for indicating one or more parameters of the ablation or probe device to a user. Moreover, the unit 301 can include a controller for processing a signal characteristic of the received photoluminescence radiation for detecting a type of bodily substance at the illuminated treatment site (e.g., to detect if a human stone is present at the illuminated treatment site). Such controller may further display a result of the processing to the user in one or more of display elements 305, may prevent emission of the ablation energy 110 depending on the detected bodily substance type, or may cause ablation energy 110 to be emitted from ablation device 101 depending on the detected bodily substance type. Further aspects of techniques to detect bodily substances will be discussed in connection with FIG. 4 below.

In the example of FIG. 3, the unit 301 is a single unit including the above discussed components. In other examples, the ablation system includes two or more units including the above described components. For example, the laser ablation source can be included in a different unit than a pilot laser. In this case, the ablation energy can be provided to the endoscope through a first waveguide while the excitation energy can be provided to the endoscope through a second waveguide.

In another example, a first unit of the unit containing the pilot laser and a second unit containing the ablation laser can be coupled so that the ablation laser radiation can be transmitted to the first unit (or so that the excitation radiation can be transmitted to the second unit). The respective first or second unit can be configured to provide both the ablation laser radiation and the excitation radiation to a port. In some examples, the ablation laser radiation and the excitation radiation can be combined in a single optical fiber (or multiple optical fibers).

An optical fiber 303 (or another waveguide) can be connected to the port 307 and to a port 304 of a handle 306 of an endoscope. The endoscope includes the handle 306 at a proximal position and a shaft 310 extending from the handle into a distal direction. The shaft 308 includes a waveguide 310 (e.g., an optical fiber) for guiding the ablation energy and the excitation energy towards a distal end of the shaft 308. In addition, the waveguide 310 can be configured to guide the emitted photoluminescence radiation from the distal tip of the shaft 308 back towards the handle 306.

In other examples, the shaft 308 includes two or more waveguides to guide the ablation energy, the excitation energy and the emitted photoluminescence radiation towards and away from the distal tip of the shaft. For example, one waveguide can be arranged to guide the ablation energy whereas a second waveguide can be configured to guide the excitation energy.

The distal tip of the shaft 308 can include a coupling structure 309 for coupling the ablation energy and the excitation energy out of the waveguide 310 to a treatment site to be ablated (e.g., a human stone). In other examples, the coupling structure can be arranged at a predetermined distance proximal of a distal tip of the shaft 308 (e.g., for coupling out the ablation energy and the excitation radiation in a lateral direction).

The coupling structure can include optical elements to condition (e.g., to focus and/or steer) the ablation laser radiation. In addition or alternatively, the coupling structure can include optical elements to condition (e.g., to focus and/or steer) the ablation laser radiation. The optical elements to condition the ablation laser radiation and the excitation radiation can be the same optical elements.

In the example of FIG. 3 the ablation laser source, the pilot laser and the radiation-receiving device are integrated in the single unit 301. In other examples, one or more of these components can be arranged in other parts of the endoscope (this is also true if the ablation laser source, the pilot laser and the radiation-receiving device are part of a different ablation device than an endoscope), For instance, the pilot laser can be integrated in the handle 306 or the shaft 308 of the endoscope. In addition or alternatively, the radiation-receiving device (e.g., a detector diode) can be integrated the handle 306 or the shaft 308 of the endoscope. In one example, the pilot laser and the radiation-receiving device can be arranged at the distal tip of the endoscope.

In the example of FIG. 3, the endoscope has a rigid shaft 308. However, the components of the medical device for ablating bodily substances discussed in connection with FIG. 3 can also be integrated in an endoscope having a flexible shaft in the same manner discussed above. Furthermore, the endoscope can be configured in a different manner than discussed in connection with FIG. 3 but still contain the medical device for ablating bodily substances discussed in connection with FIG. 3. For instance, the endoscope can contain additional elements in addition to a shaft and a handle. For example, the endoscope can include elements of an endoscope known in the art (e.g., an imagining device for providing an image of a treatment site). In addition or alternatively, the ports for providing the ablation energy and the excitation energy can be arranged at different locations than the handle of the endoscope (e.g., a dedicated coupling element distal of the handle).

Photoluminescence Signals of Human Stones

In connection with FIGS. 4 to 12 example methods for detecting human stones will be discussed. Different measurement setups for measuring a photoluminescence radiation (for example, fluorescence radiation), emitted by human stones will be discussed first in connection with FIG. 4 to FIG. 6. Even though these setups were used to measure the photoluminescence radiation ex vivo, the components of the measurement setups can also be integrated in the medical devices of FIG. 1 to FIG. 3. Subsequently, experimental data of different human stones and other bodily substances will be presented in connection with FIG. 7 to FIG. 11. Last, different methods for detecting human stones will be discussed in connection with FIG. 12.

Experimental Results

In the following section experimental data of ex vivo experiments which demonstrate that human stones can be detected by using the methods described in the present disclosure will be presented. The ex vivo experiments closely reproduce the situation in vivo regarding optical properties of the employed material.

Samples

Forty-two human urinary stones that had been extracted from patients over a period of about twelve months were stored in phosphate buffered solution (calcium, magnesium, antifungal agent and antibiotics added) at T=4° C. Calculous composition of 35 samples was verified by NIR Fourier transform spectrometry. The substances of the stones were carbon oxalate monohydrate, carbon oxalate dihydrate, apatite, magnesium ammonium phosphate hexahydrate (struvite), calcium hydrogenphosphate dehydrate (brushite) and carbonate apatite and uric acid. Porcine renal calix and ureter (slaughter material) were utilized as tissue samples either directly after removal or after storage at T=−18° C.

Set-Up and Radiation Sources

Figure 4:
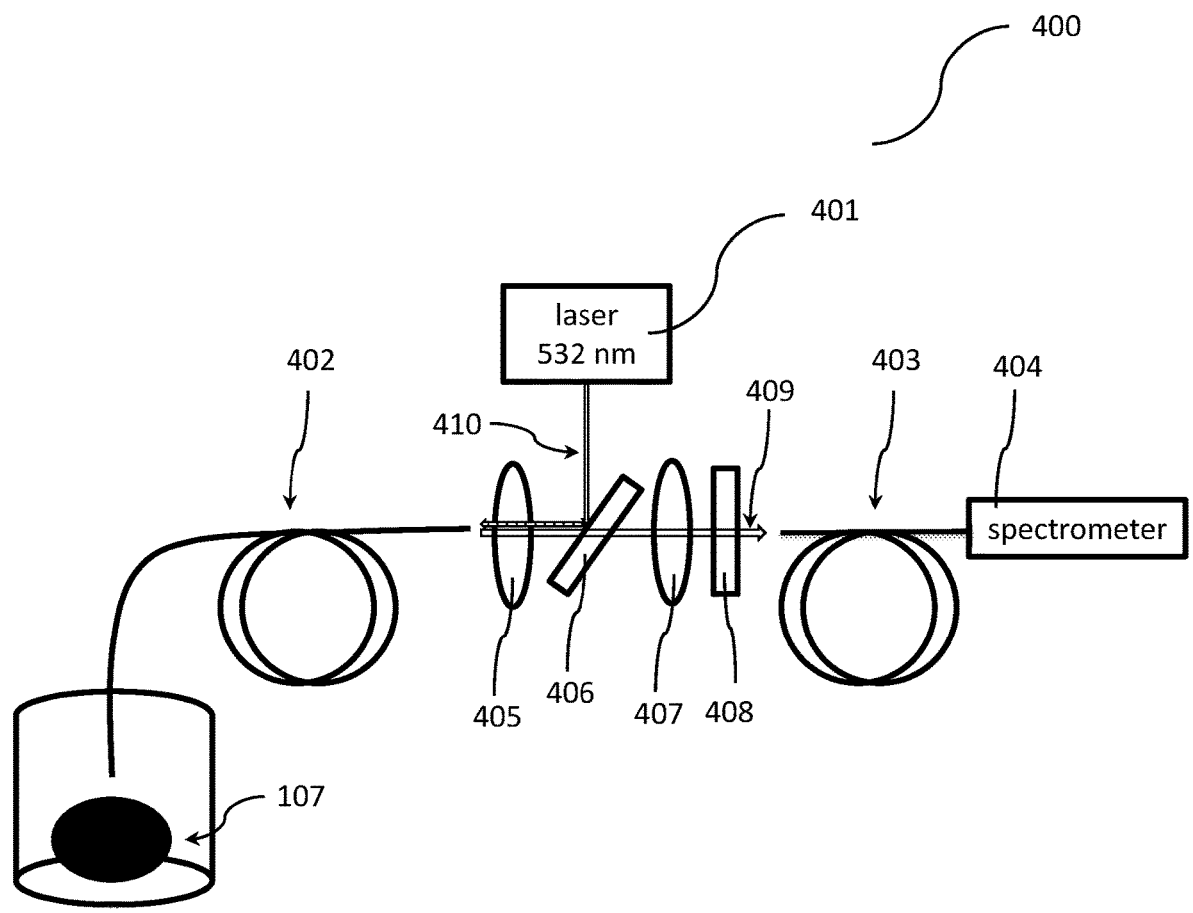
FIG. 4 depicts a measurement setup for measuring photoluminescence spectra according to the present disclosure.

A set-up for fiber-based photoluminescence measurements is shown in FIG. 4: the excitation radiation source 401 was coupled into the probe fiber via a dichroitic mirror 406 (in the example of FIG. 1 a dichroic laser beam combiner 552 nm by Edmund Optics having >98% reflection between 514 nm and 543 nm and >95% transmission between 561 nm and 790 nm). The excitation radiation was coupled into fiber 402 by the dichroitic mirror 406 and guided towards the human stone sample. The emitted photoluminescence radiation 409 was collected by fiber 402 passed the dichroitic mirror 406 and was guided to a grating spectrometer 404 (AvaSpec-3648-USB2, grating 330-850 nm manufactured by Avantes) via another quartz fiber 403 (having diameter of 200 pm). Residual excitation light was suppressed by a long pass filter 408 in the detection light path (Schott OG 550, Edmund Optics). The setup also included suitable passive optical elements for coupling the radiation into fibers 402 and 403 (e.g., a lenses 405 and 407).

Even though the setup of FIG. 4 was used for experimental measurements ex vivo, this setup can also be integrated in a medical device (e.g., the devices as discussed above in connection with FIG. 1 to FIG. 3). In one example, the excitation radiation source 401 (as part of the probe device), the grating spectrometer 404 (as part of the radiation-receiving device) and the passive optical components 405-408 can be integrated into an unit 301 as shown in FIG. 3. In addition, even if the setup of FIG. 4 includes particular components, a medical device implementing this setup can also be equipped with different components for the same tasks (e.g., different fibers, different passive optical components or a different spectrometer). In general, the components discussed above in connection with FIG. 1 to FIG. 3 might replace a respective components of the setup of FIG. 4. Moreover, even though the setup of FIG. 4 includes free-space optics, corresponding fiber-optic elements can be used (e.g., a coupler for coupling the excitation radiation 410 into fiber 402).

In a first series of measurements (depicted in FIG. 5), a diode pumped passively Q-switched laser (532 nm) was used for fluorescence excitation (FTSS 355-50 at 1 kHz by Cry-Las). At a repetition rate of f=1 kHz, pulse duration was T=1.2±0.05 ns (as measured with a photodiode UPD-200-UP by AlphaLas, and a digital oscilloscope DPO 70604 6 GHz, 28GS/s by Tektronix). Pulse energy at the output of the 600 μm diameter low-OH quartz probe fiber (of type Light-Trail by StarMedTec) was E=36.5±1 mJ (as measured with a pyroelectric energy sensor PE 10-SH-V2 by Ophir).

Photoluminescence radiation signals were collected on eight sites of the artificial stone (integration time CCD array of the spectrometer was 50 ms), five to seven points on fifteen patient samples (82 curves overall, integration time was 50 ms), sixteen sites of a porcine renal calix (integration time 500 ms and 1 s, respectively) and ten sites of the porcine ureter (integration time was 1 s). Tissue samples for this experiment were used directly after removal. For all measurements, the probe fiber 402 was either held in contact with the specimen or at a distance <1 mm. To enable comparing spectra taken with different integration times, all curves were normalized to the signal at a wavelength of 532 nm.

The excitation source was then changed to a low power continuous wave 532 nm-module (CW532-005F by Roithner Lasertechni k having P<5 mW and a TEM00 beam profile). The output power as measured at the output of a d=230 μm quartz fiber 403 was P=0.41±0.07 mW (LM-2 VIS by Coherent). 139 fluorescence values were taken on all 42 patient samples (three to ten points each sample, integration time was 200 ms). Four curves were recorded on a defrosted porcine renal calix (integration time 100 ms).

Figure 5:
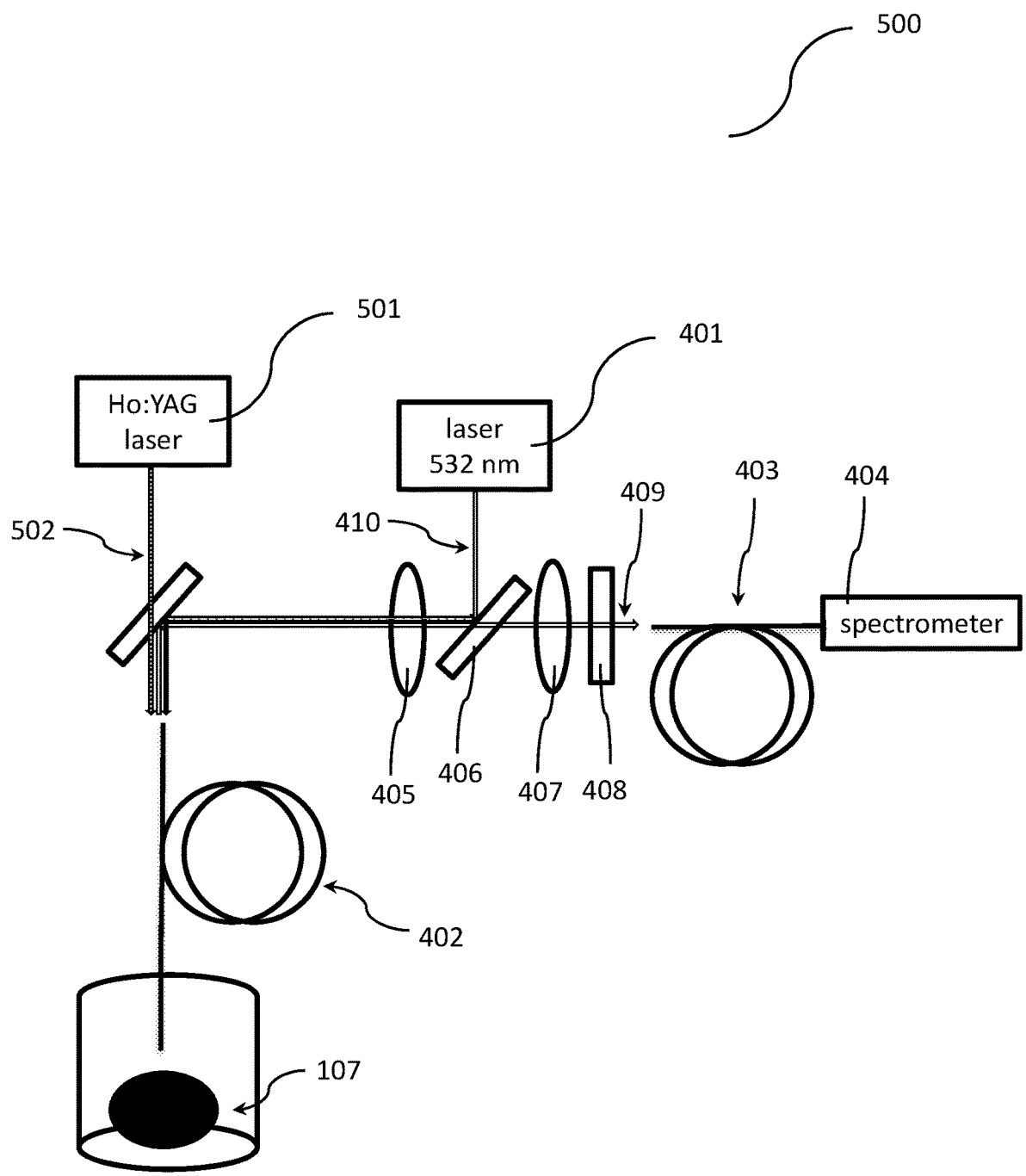
FIG. 5 depicts a measurement setup combining an ablation laser source and a probe device according to the present disclosure.

The experimental set-up was extended (as shown in FIG. 5) with another dichroic mirror 502 reflecting the excitation and photoluminescence light while transmitting the beam of a Ho:YAG ablation laser source 501 (Auriga XL by StarMedTec operating at a wavelength of 2100 nm at a repetition rate of <30 Hz and a power of 50 W, pulse duration was between 100 µs and 800 µs). The low-OH quartz probe fiber 402 had a diameter of d=600 µm (of type LightTrail by StarMedTec), the fiber 403 connected to the spectrometer 404 had a diameter of 365 µm (of type Light-Trail by StarMedTec). The laser pulse energy for lithotripsy was E=240±50 mJ at a repetition rate of 10 Hz, With an excitation power of P=0.45 mW (CW532-005F by Roithner Lasertechnik), several spectra on one human calculi were taken in between/while firing the Ho:YAG laser (integration time of 200 ms).

Figure 6:
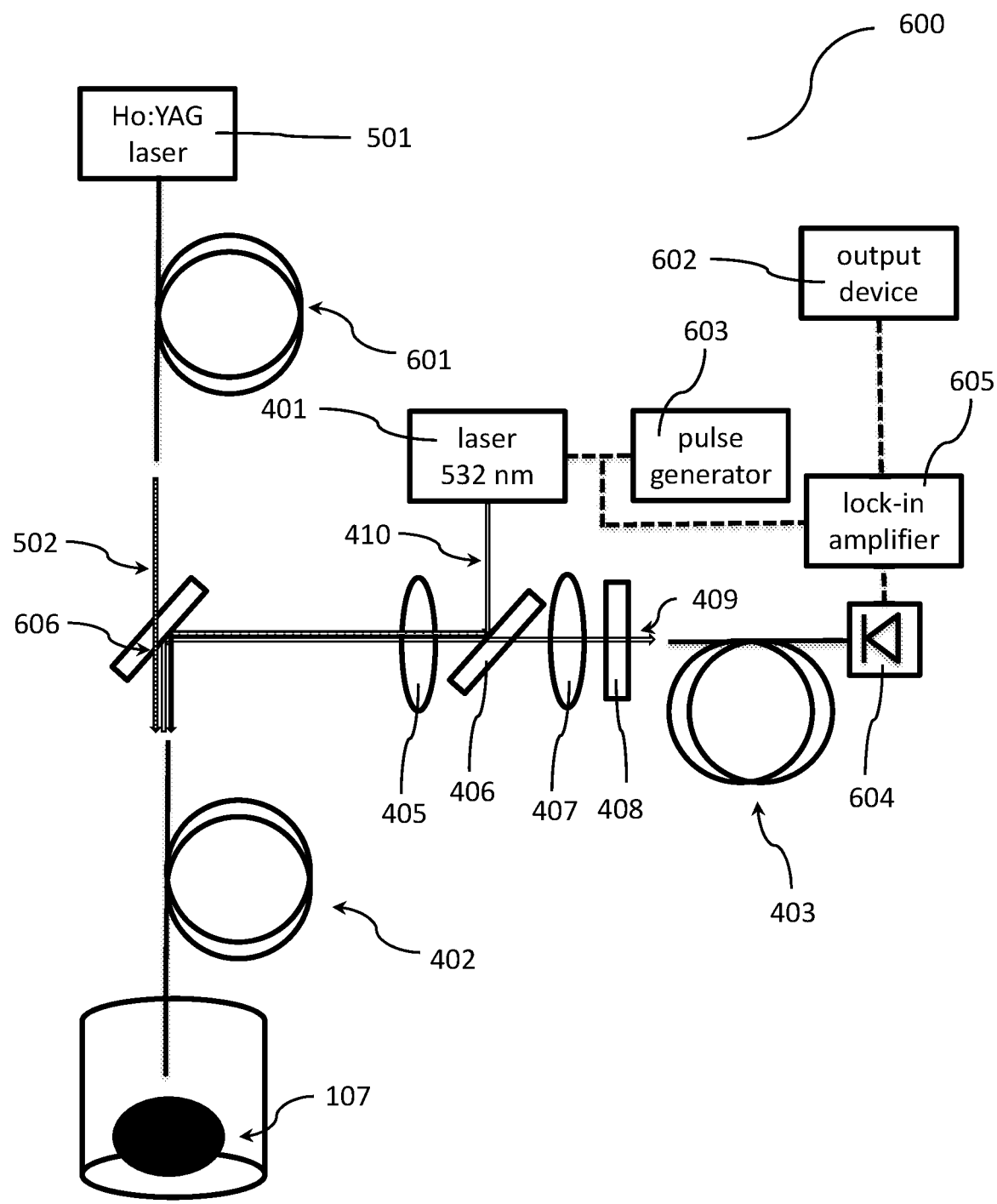
FIG. 6 depicts another measurement setup combining an ablation laser source and a probe device according to the present disclosure.

With a similar optical set-up (as shown in FIG. 6), a lock-in-measurement was implemented to get insensitive to background light: A 532 nm-diode laser module 401 (Flex-point FR-53/1AAF-AV-SD-PE by Blau Optoelektronik having an output power of P=1 mW) was modulated via a pulse generator 603 (UPG100, EQ-3). This pulse generator 603 delivered a rectangular function with an on and off time of t=7.58 ms each, i.e. a modulation frequency of f=66 Hz. The average power at the output of the probe fiber was P=0.31±0.02 mW (measured by LM-2 VIS by Coherent). In the photoluminescence light path, the excitation light 410 was suppressed via two dichroitic mirrors 406 and 606: the first one 606 transmitting at a wavelength of 532 nm (T>95% 532 nm and 2100 nm, R>90% between 560 nm and 850 nm), the second one 406 reflecting at a wavelength of 532 nm (dichroic laser beam combiner 552 nm by Edmund. Optics: >98% reflection between 514 nm and 543 nm and >95% transmission between 561 nm and 790 nm). The photoluminescence light was coupled into a fiber 403 (d=200 µm) whose end was bolted to the SMA-adapter of a photodiode 604 (DET10A by Thorlabs). Reference and signal input of a lock-in amplifier 605 (LIA-MV-150-S, FEMTO) was connected with the pulse generator 603 and photodiode 604 signals. Sensitivity was set to 100 pV, a time constant to 300 ms. The probe fiber 402 had a diameter of 365 µm (LightTrail by StarMedTec). Six stone samples (randomly chosen from the collection of 42; five points each sample) and the skin of the inner side of a human arm (three points) were used as samples. White light background was delivered by lab illumination (fluorescence lamps—not shown in FIG. 6) and a Xenon light source (5133 Combilight PDD, Wolf—also not shown in FIG. 6).

As already discussed in connection with FIG. 4, the setups of FIG. 5 and FIG. 6 can also be integrated in a medical device (e.g., the devices as discussed above in connection with FIG. 1 to FIG. 3). In one example, the excitation radiation source 401 and the pulse generator 603 (as part of the probe device), the photodiode 604 and the lock-in amplifier (as part of the radiation-receiving device) and the passive optical components 405-408 and 606 can be integrated into in unit 301 as shown in FIG. 3. Moreover, the ablation laser source 501 can be also integrated in unit 301 as shown in FIG. 3, or in a separate unit.

In addition, even if the setups of FIG. 5 and FIG. 6 includes particular components, a medical device implementing this setup can also be equipped with different components for the same tasks (e.g., different fibers, different passive optical components or a different photodetector). In general, the components discussed above in connection with FIG. 1 to FIG. 3 might replace a respective components of the setups of FIGS. 5 and 6. Moreover, even though the setups of FIGS. 5 and 6 includes free-space optics, corresponding fiber-optic elements can be used (e.g., a coupler for coupling the excitation radiation 410 into fiber 402).

Measurement Data

Figure 7:
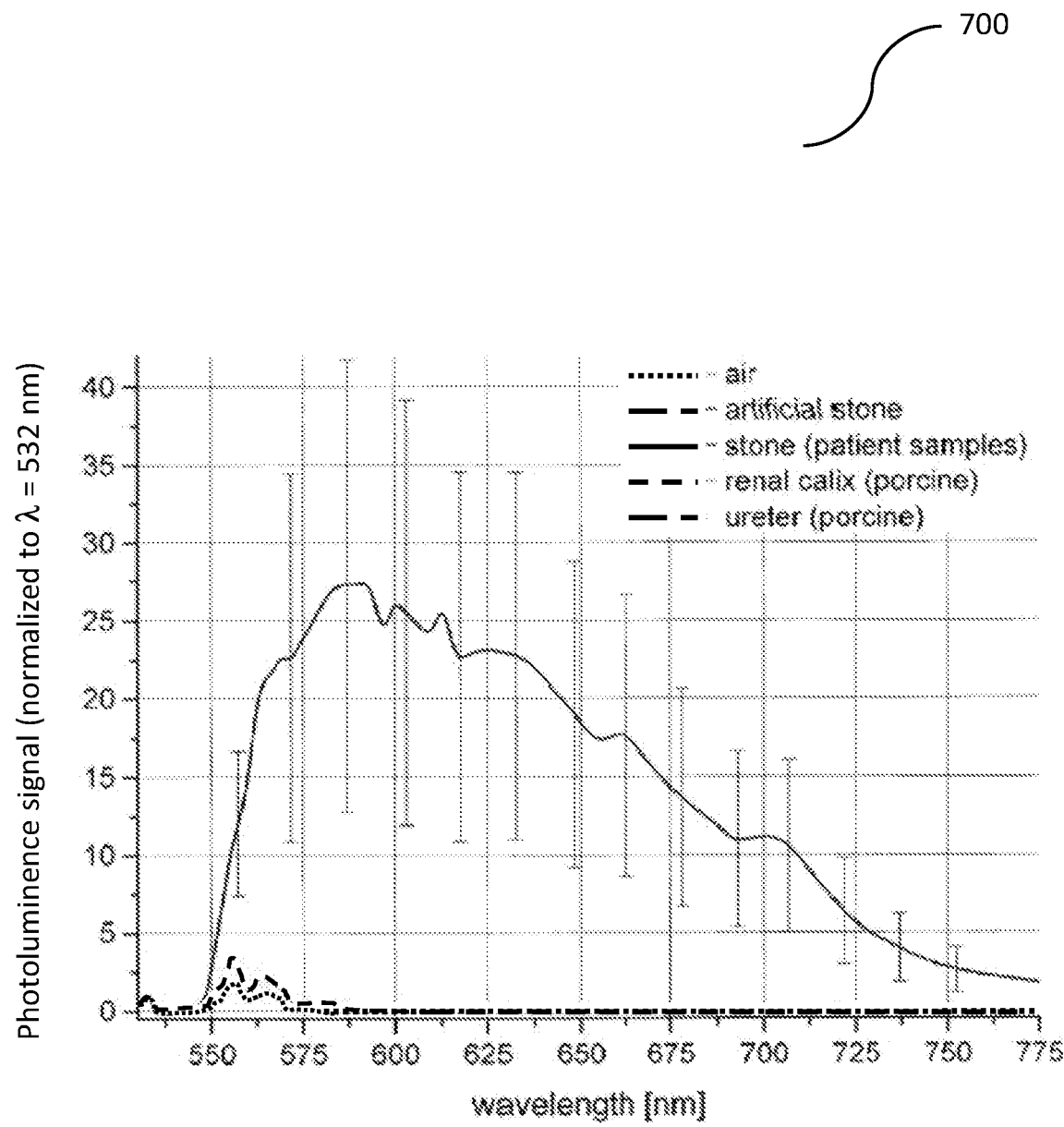
FIG. 7 shows example photoluminescence spectra inn response to pulsed excitation according to the present disclosure.

FIG. 7 shows the results of the pulsed excitation measurement series. To be able to compare data taken with different spectrometer integration times, all curves were normalized to the residual excitation light at 532 nm. The normalized photoluminescence signal of fifteen human stone samples is 27±15 at about 590 nm where the fluorescence signal has its maximum. The 'lowest' of the 82 curves taken on those specimens had a value of 1.95 at this point. Overall, only five curves had values lower than seven. Porcine renal calix and ureter give a signal that is not significantly different from the background (fiber held in air): the normalized signal at a wavelength of 587 nm is <0.5. The same is the case for artificial stone. Thus, human stones can be discriminated from other bodily substances by monitoring photoluminescence radiation emitted from a treatment site generated by pulsed radiation.

Figure 8:
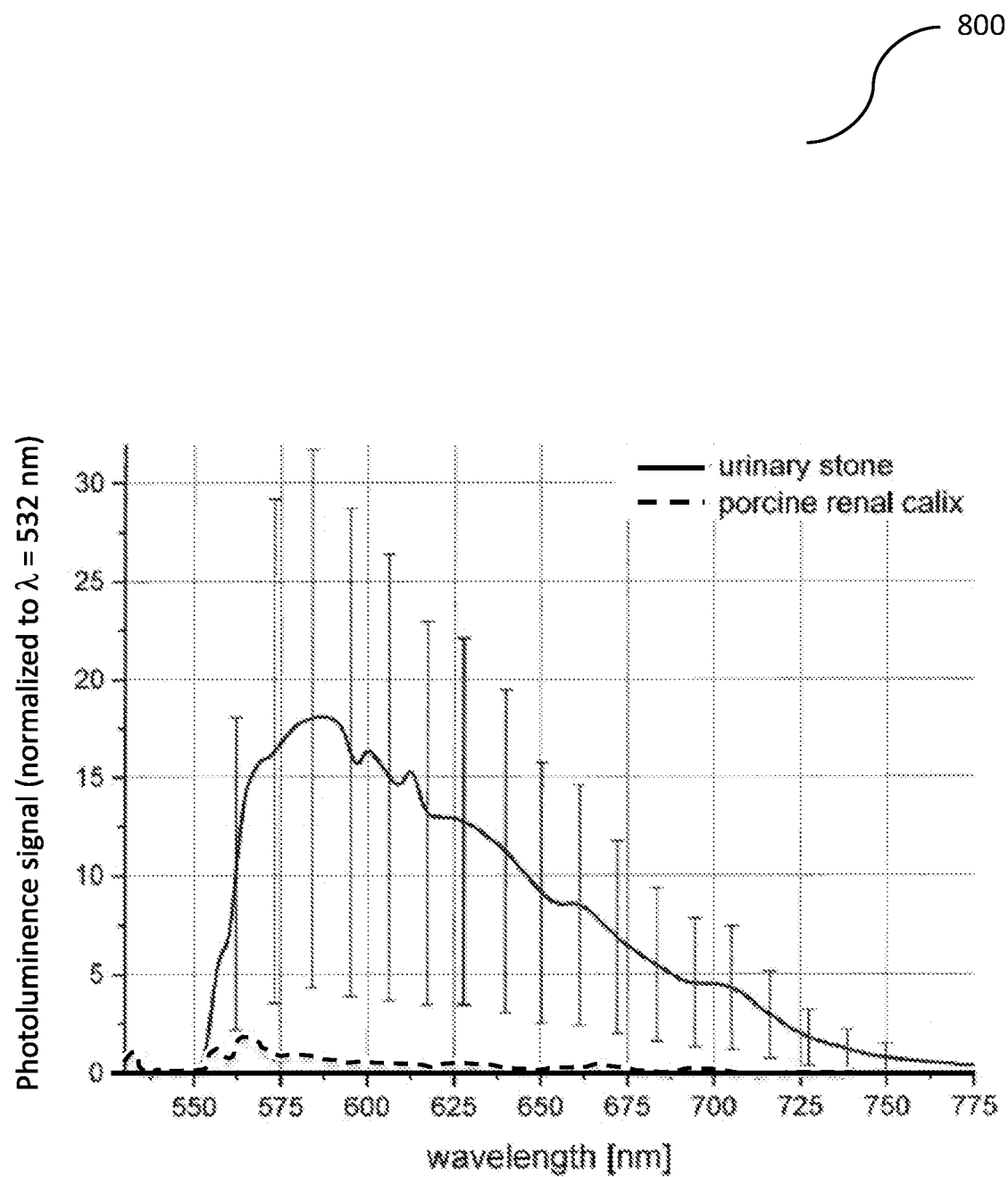
FIG. 8 shows example photoluminescence spectra in response to continuous wave excitation according to the present disclosure.

As can be seen in FIG. 8, with low power continuous wave excitation (P<0.5 mW) urinary calculi gave a strong signal of 18±14 at a wavelength of 587 nm when the curves where normalized to the signal at a wavelength of 532 nm. The smallest stone value (at a wavelength of 587 nm) was 1.05. All points measured on a porcine calix were <1 (0.74±0.1). Again, human stones can be discriminated from other bodily substances by monitoring photoluminescence radiation emitted from a treatment site generated by (comparatively low power) cw radiation.

Figure 9:
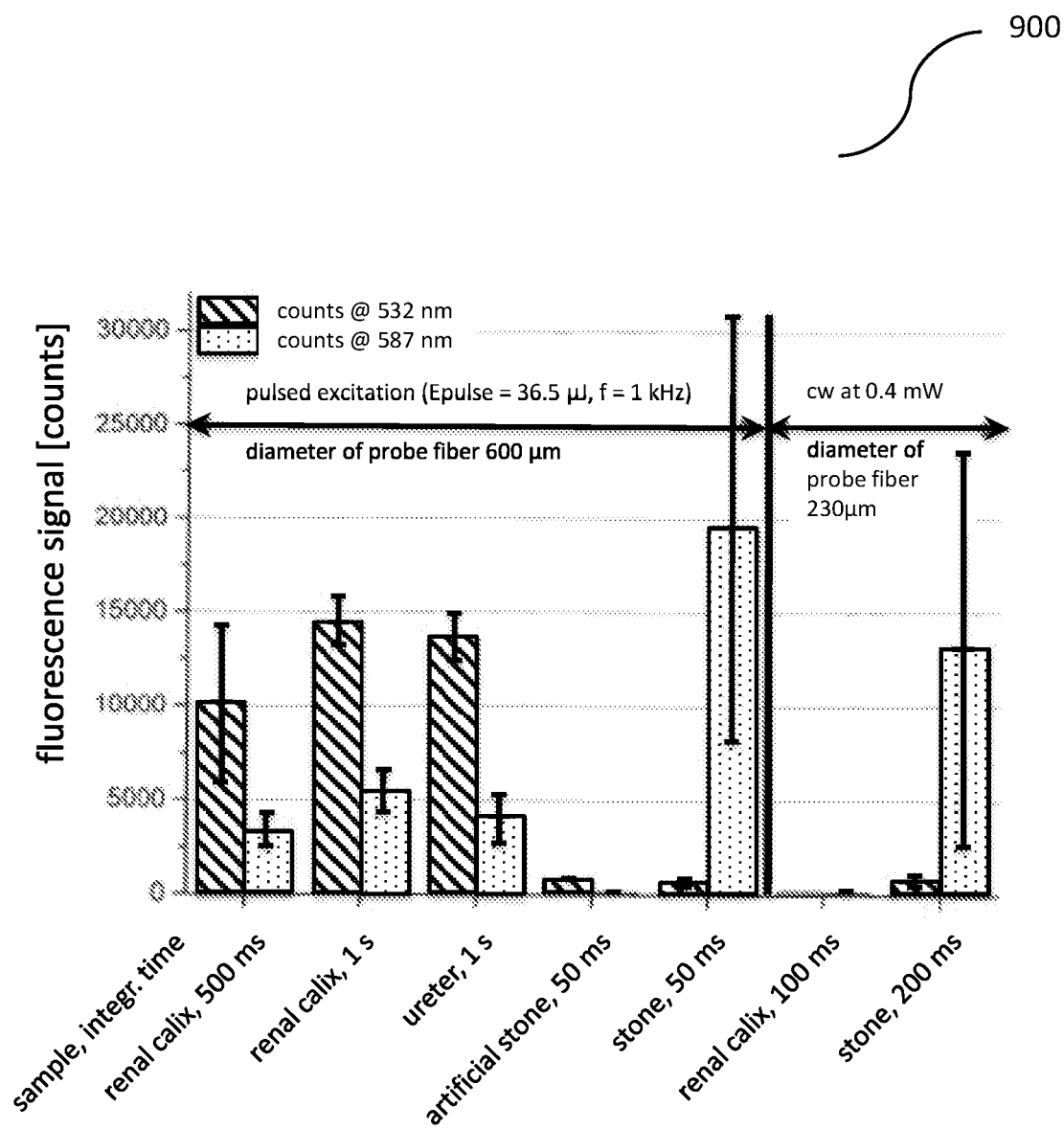
FIG. 9 shows curves illustrating a relationship of photoluminescence response at different wavelengths according to the present disclosure.

Looking at the raw data of the pulsed and cw measurement series, one finds that the relation between average excitation power, integration time (of the spectrometer's CCD array) and fiber diameter is not linear: FIG. 9 depicts the raw counts of the measurements at two wavelengths (at a first wavelength of 532 nm and at a second wavelength of 587 nm). Comparing e.g. the counts for pulsed excitation of renal calix, doubling the integration time from t=500 ms to t=1 s did not result in a count number twice as high (but a factor 1.4 at a wavelength of 532 nm and a factor of 1.6 at a wavelength of 587 nm). The average excitation power was P=36.5 mW with the pulsed laser and P=0.4 mW with the cw source. Taking this factor of ~90 and dividing by a factor of four due to the longer integration time with the cw measurement of urinary stones, with a linear relationship (neglecting the different fiber diameters: 600 µm for pulsed experiments and 230p µm for cw measurements), count numbers should be a factor of about 23 higher for renal calculi, pulsed excitation than for cw excitation.

Figure 10:
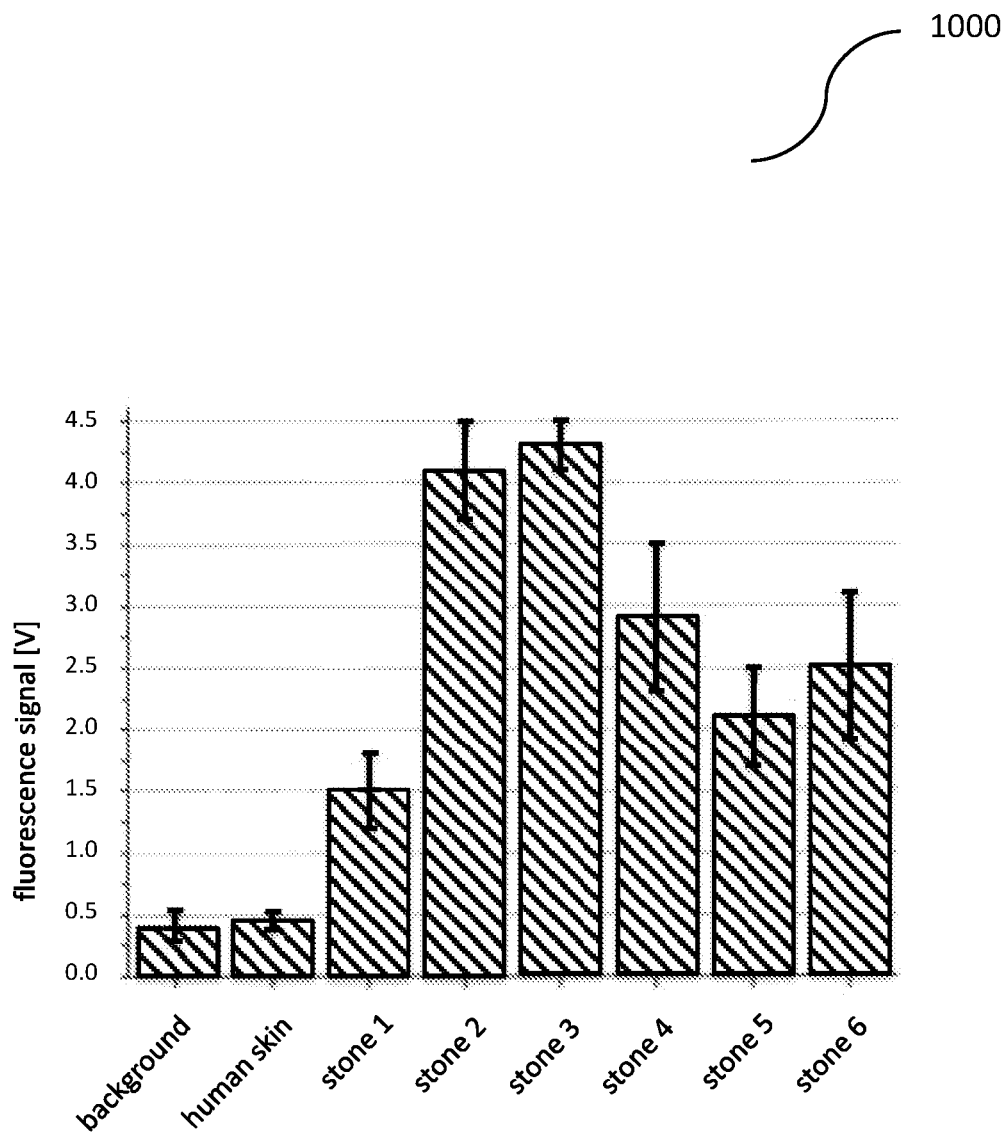
FIG. 10 shows example photoluminescence signals retrieved by using a lock-in-amplifier according to the present disclosure.

However, the number of counts do not differ significantly, neither at a wavelength of 532 nm (650±230 pulsed, 770±340 cw) nor at a wavelength of 587 nm (19600±11300 pulsed, 13200±1 0500 cw). But even though the normalization to the number of fluorescence counts at a wavelength 5.32 nm does not eliminate the differences due to varying excitation power, integration times and fiber diameters and therefore does not give quantitatively exploitable numbers, FIG. 10 shows that qualitatively the result is correct: the ratio of the counts at a wavelength of 587 nm to the counts at a wavelength of 532 nm is <1 for all tissue samples (and the artificial stone), but much larger than 1 for human urinary stones.

A test of the measurement principle during lithotripsy showed that, as reported in prior publications strong luminescence signals appear when Ho:YAG pulses are fired on a human stone. However, this did not happen with all pulses, but irregularly.

With the lock-in set-up (as shown in FIG. 6, cw excitation, photodiode detection), the background signal was U=400±130 mV (as output lock-in amplifier) even with bright white light illumination (Xenon light source). Six stone samples gave values of U=1.5±0.3 V to 4.3±0.2 V which are a factor of 3 to 9.5 higher than a skin signal U=450±70 mV. These results are summarized in FIG. 10.

Stone Detection Methods

As can be seen in diagrams of FIG. 7 to FIG. 10, human stones can be discriminated from other bodily substances (e.g., tissue) by the techniques described in the present disclosure. In particular, a probe device emitting excitation radiation at a comparatively low energy can be used to generate a sufficient photoluminescence signal for human stone detection and discrimination. These low energy levels can be selected so that no tissue is damaged at the treatment site.

In the present disclosure, the expression "no tissue is damaged at the treatment site" does not exclude any physiological modification of tissue by the excitation radiation (e.g., microscopic lesions or modifications). It is understood that non-harmful modifications to bodily substances are not considered as "damage" even if tissue is permanently modified. Rather, the term "damage" refers to modifications (e.g., destruction) of tissue that can lead to short term or medium term complications. For example, macroscopic ablation of tissue is considered to be a damage to tissue at the treatment site. In other examples, perforation of bodily vessels (e.g., of the vessels of the urinary system) is considered to be a damage to tissue at the treatment site. Even though the parameters of the excitation radiation which can cause damage depend on the particular treatment site, the particular treatment modalities and the particular treatment device it is nevertheless possible to determine a parameter range (e.g., wavelength, pulse duration, illumination time and energy) of the excitation radiation which does not cause damage to tissue for the respective application case.

For instance, excitation radiation at energy levels that does not exceed a maximum permissible radiation for irradiating human skin as set out in DIN EN 60825-1:2012-11 can be considered as excitation radiation which does not damage tissue at the treatment site. In other examples, energy levels below 50 mJ/s. preferably below 20 mJ/s, more preferably below 1 mJ/s can be considered as energy level that does not exceed a maximum permissible radiation for irradiating human skin.

Moreover, using a phase-sensitive detector can further improve the human stone detection techniques. Further aspects of phase-sensitive detection processes are discussed below.

Figure 11A:
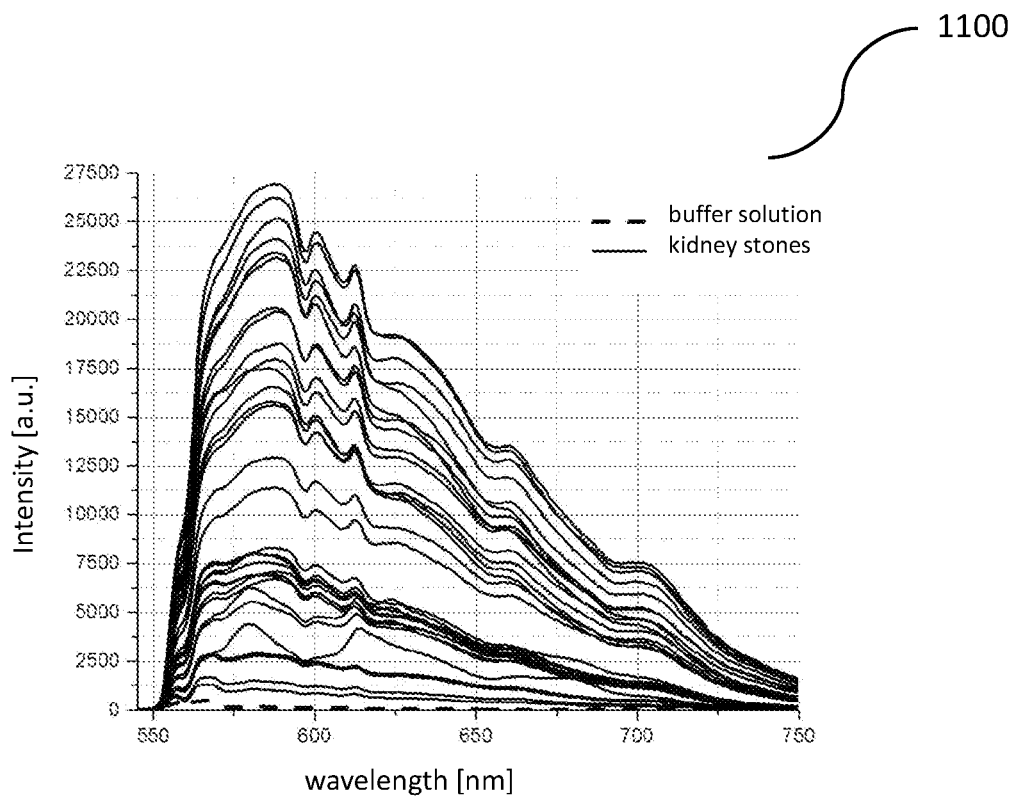
FIG. 11a and FIG. 11b show example photoluminescence spectra according to the present disclosure.

FIG. 11a shows further example photoluminescence spectra (solid lines) of different human stone samples (examined ex vivo) and a reference measurement of a buffer solution (dashed line). In the example of FIG. 11a, the photoluminescence signal has been generated by illuminating the human stone samples by laser excitation radiation of frequency doubled solid state laser emitting continuous wave laser radiation at 532 nm (as in the setup of FIG. 5). The mean power of the laser excitation radiation was below 1 mW (which is below a laser power admissible by regulatory requirements for irradiation of the skin). As can be seen in FIG. 11a, the photoluminescence signal of the human stone samples is considerably larger than a photoluminescence signal of the reference sample. Thus, an intensity of emitted photoluminescence radiation of a treatment site illuminated by the low-power (e.g.; below 5 mJ/s) laser radiation can be used for discriminating between human stones and other bodily substances (e.g., tissue).

In some examples, the relatively large photoluminescence signal of the human stone samples can be due to the particular organic matrix of the kidney stones (at least some artificial stones do not show a comparable photoluminescence behavior). A similar behavior as shown in FIG. 11a can also be found in bile stone samples.

Even though in the example of FIG. 11a shows excitation by a green continuous wave laser at mean power below 1 mW, other excitation source parameter can also be used in the medical devices of the present disclosure. For example, a laser source at a different wavelength can be employed to generate the excitation radiation. For example, a probe device can be configured to deliver excitation energy at a wavelength in the range between 380 and 900 nm (e.g., in the wavelength range between 480 and 620 nm, preferably between 500 and 550 nm). In addition or alternatively, the probe device can deliver the excitation radiation at below 50 mJ/s. preferably below 20 mJ/s, more preferably below 1 mJ/s. In some examples, an output level of the laser source can be greater and reduced before delivered to the treatment site (e.g., by dedicated attenuation elements or by losses of the guiding elements). In addition or alternatively, the laser source of the probe device can be pulsed (for instance pulsed at repetition rates between 100 Hz and 10 KHz and a pulse length between 100 ps and 100 ns).

In other examples, the laser source is configured to deliver the excitation radiation at an energy level that does not exceed a maximum permissible radiation for irradiating human skin as set out in DIN EN 60825-1:2012-11.

Moreover, even though the laser used to generate the photoluminescence signal of FIG. 11a is a solid state laser, the medical devices of the present disclosure can include different types of lasers (e.g., a fiber laser or a semiconductor laser). In other examples, a light emitting diode can be used to illuminate a treatment site in the medical devices of the present invention. The peak power values discussed in the present disclosure can easily be achieved by light emitting diodes. In other examples, still different excitation radiation sources (e.g., a gas discharge lamp) can be employed to generate the excitation radiation.

In one example, radiation energy to generate the photoluminescence signals shown in FIG. 11a can be provided by a pilot laser of a medical device for ablating tissue.

Phase-Sensitive Detection

Figure 11B:
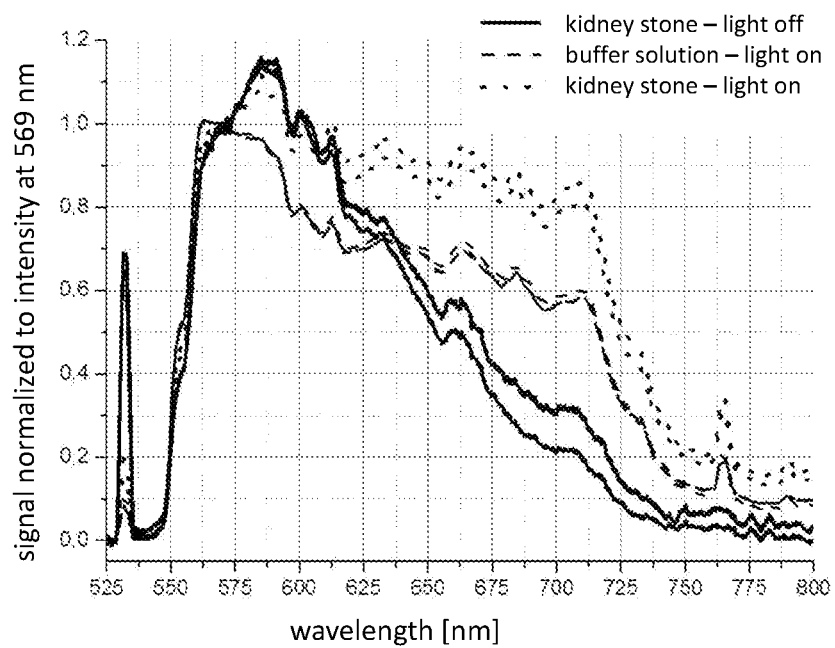

FIG. 11b depicts photoluminescence spectra of a kidney stone sample and a buffer solution with and without white light illumination by a lamp of the type frequently used during endoscopic surgery to image the endoscopic device. The white light source can generate a signal which can be a multiple of the photoluminescence radiation typically emitted by human stones. Therefore, a detection of the photoluminescence signal of the human stones might be difficult under white light illumination conditions.

The medical devices of the present disclosure can use phase sensitive detection techniques to improve a signal-to-noise ratio of the detection process (as already discussed above). In this manner, a photoluminescence signal generated by a human stone can also be detected in the presence of white light illumination during an endoscopic treatment. However, the improvement of the signal-to-noise ratio can also be advantageous to deal with other noise sources than a white light lamp.

In one example, the radiation-receiving device includes a lock-in amplifier. The lock-in amplifier is configured to process an input signal (i.e., a signal generated in response to radiation reflected back through an endoscope from a treatment site, multiply the input signal by a reference signal (either provided from the internal oscillator or an external reference source), and integrate the resulting signal over a specified time (e.g., in the order of milliseconds to several seconds). The resulting signal is a DC signal, where the contribution from any signal that is not at the same frequency as the reference signal is attenuated (ideally close to zero). As, e.g., a signal due to white light illumination by a lamp is substantially a DC signal, the lock in amplifier of the radiation-detection device can greatly attenuate the influence of this signal.

If a phase-sensitive detector (e.g., a lock in amplifier) is included in the radiation detection device, the probe device (e.g., a probe laser source) is configured to generate a modulated excitation energy signal. In one example, the excitation energy signal can be intensity modulated. For instance, an intensity-modulated signal can be a pulsed signal pulsed at a predetermined frequency. In other examples, an excitation energy signal can be over-modulated (e.g., by a sinusoidal modulation). It is merely required to provide a substantial amount of the energy of the excitation radiation at or near a particular frequency.

Alternatively or in addition, other techniques than phase-sensitive detection can be employed to detect a photoluminescence signal of a particular type of bodily substance (e.g., a human stone). For instance, a medical device can be configured to perform one or more reference measurements while the excitation energy is switched off and normalize a signal detected when the excitation energy is delivered by the one or more reference measurements. In this manner, a contribution of a white light lamp used during an endoscopic procedure, or other ambient light sources, can be reduced.

In other examples, known sources of stray light (e.g., a white light source in an endoscopy operation) can be switched off during bodily substance detection.

In addition or alternatively, the medical device can be configured to average a detected signal over a predetermined period of time. In this manner, random fluctuations in the detected signal can be reduced or cancelled.

Example Methods of Bodily Substance Detection

In the subsequent sections, example methods for bodily substance detection will be discussed in connection with FIG. 12. The methods described in the following can be carried out by a medical device for ablating bodily substances (e.g., the devices described in connection with FIG. 1 or FIG. 3).

Figure 12:
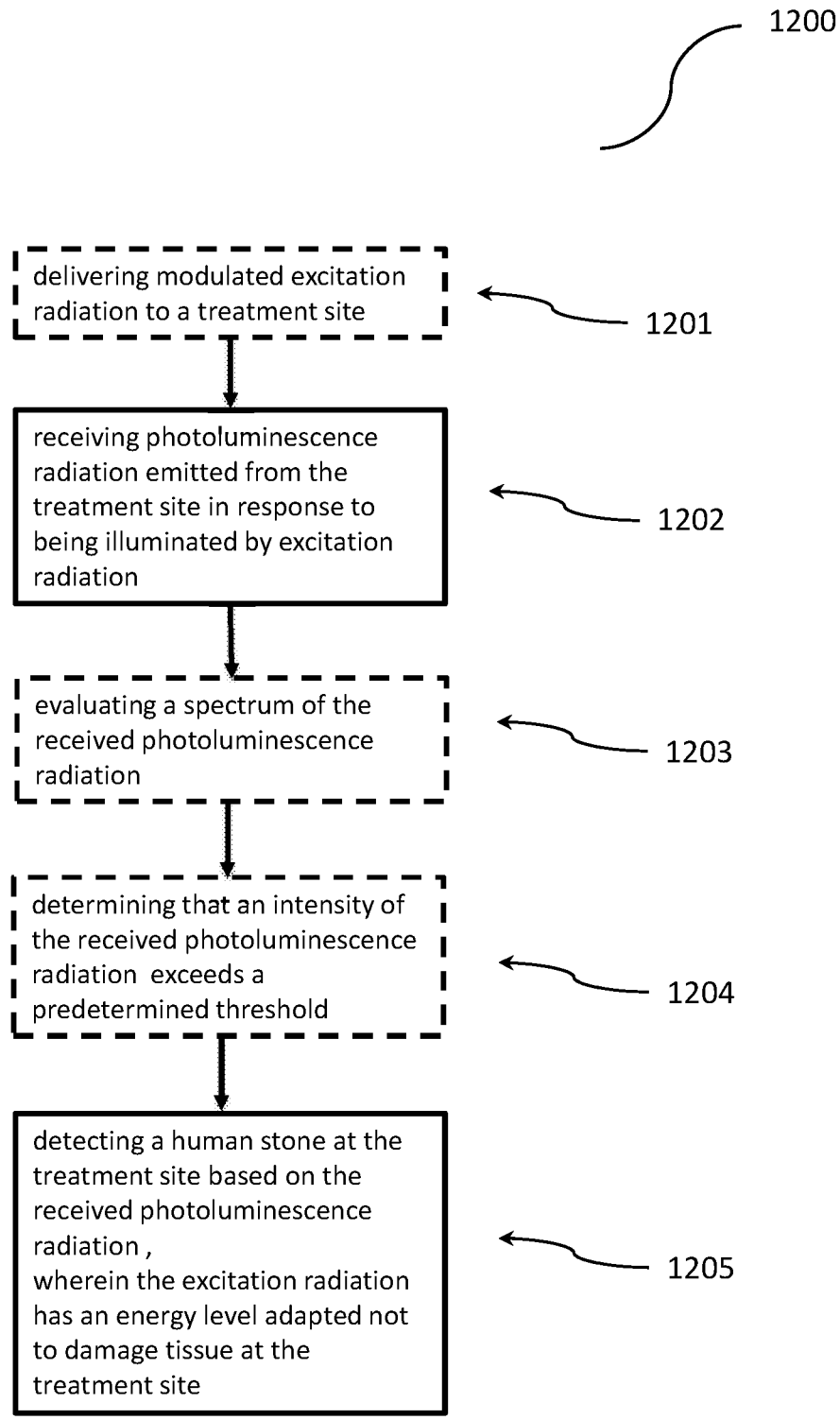
FIG. 12 depicts the steps of example of detecting a human stone in vivo according to the present disclosure.

As shown in FIG. 12, a method of detecting a human stone in vivo can include delivering 1201 excitation light to a treatment site, receiving 1202 photoluminescence radiation emitted from the treatment site in response to being illuminated by the excitation radiation and detecting 1205 a human stone in the treatment site based on the received photoluminescence radiation, the excitation radiation delivered at the treatment site having an energy level adapted not to damage tissue at the treatment site.

In one example, the method includes determining that an intensity of the received photoluminescence radiation exceeds a predetermined threshold. If an intensity of the received radiation exceeds the predetermined threshold, it can be determined that the treatment site includes a human stone (e.g., a kidney stone or a bile stone). If the intensity of the received radiation does not exceed the predetermined threshold, it can be determined that the treatment site does not include a human stone.

In one example, all radiation reflected back from a treatment site can be evaluated for human stone detection. For example, a single intensity value can be determined (effectively integrating over all wavelengths contained in the back reflected signal). In this case (and in general), a wavelength of the excitation radiation can be filtered from the received signal (e.g., by employing a band-stop filter).

In other examples, the radiation reflected back from a treatment site can be evaluated only partially for human stone detection. For instance, a portion of the received radiation can be filtered (e.g., by using a high-pass, low-pass or a band-pass filter). In the example of FIG. 11a, it can be seen that the photoluminescence response of kidney stones can be particularly high in particular wavelength ranges. Therefore, in some examples the medical device includes a filter for blocking all radiation outside a predetermined wavelength range suitable for kidney stone or bile stone detection. The filters described herein can be separate components (e.g., an absorbing or reflecting coating acting as a filter). In other examples, the filtering function can be provided by the fiber-optic components used to guide the photoluminescence radiation (e.g., components having a particular transmission function).

In other examples, the human stone detection technique includes evaluating multiple wavelength ranges. For instance, a ratio of a received intensity in a first wavelength range and a second wavelength range can be used for human stone detection.

In still other examples, a received radiation can be measured in a spectrally resolved manner. A spectrum of a received radiation can be compared to one or more reference photoluminescence spectra of human stones for human stone detection. However, as also discussed above, no spectrally resolved measurement is required for human stone detection when using the techniques of the present disclosure. For instance, a single intensity value (e.g., in a predetermined wavelength band as described above) can suffice for human stone detection.

The characteristics of the received radiation can be determined as one or more parameters of the received radiation. The detection of a human stone in the sampled treatment site can include evaluating the one or more parameters. For instance, a parameter can be an intensity of a received radiation in a predetermined wavelength range (e.g., an intensity at 590 nm).

The techniques described herein can be used to detect if a human stone is present in a treatment site. In general, as discussed above, human stone detection can involve digitally classifying the received radiation based one or more parameters of the received radiation (in the classes "no stone" vs "stone").

However, the techniques of the present disclosure can also be used to determine a distance between a human stone and a medical device for ablating bodily substances (e.g., a distal type of the medical device for ablating bodily substances). In one example, a distance between a human stone and the medical device can be detected based on a level of intensity of a received photoluminescence signal. In one example, the higher a level of an intensity of a received photoluminescence signal the smaller a distance between the medical device and the human stone.

As discussed above, the techniques of the present disclosure can be used to avoid delivering ablation energy to bodily substances other than human stones. However, if a distance between the medical device and a human stone can be determined (e.g., by evaluating a level of intensity of a received photoluminescence signal), a user of the medical device can also bring the medical device in a position for human stone ablation (e.g., as close as possible to the human stone or to a predetermined distance to the human stone). The medical device can be configured to provide feedback to a user regarding a distance between a human stone and the medical device (e.g., an audio feedback or a visual feedback).

Moreover, the techniques described herein can also be used during delivery of ablation energy (e.g., ablation laser energy). Even though the ablation energy can also elicit a substantial photoluminescence response in a human stone, a human stone can still be reliably detected as a signal strength of the emitted photoluminescence response is increased. For instance, if human stone detection involves comparing a received photoluminescence signal to an intensity threshold, additional radiation generated by ablation energy will not disturb a determination process.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Further, as used herein, the terms "about," "substantially," and "approximately," may indicate a range of values within +/−5% of a stated value.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A medical laser system, comprising:
a first laser source configured to generate a treatment radiation;
a second laser source configured to generate an excitation radiation in a pulsed manner;
a radiation detector;
an optical system configured to:
optically couple the treatment radiation and the excitation radiation into a fiber, and
optically couple photoluminescence radiation received at a distal end of the fiber to the radiation detector, wherein the photoluminescence radiation is emitted by a target responsive to illumination by the excitation radiation; and
a controller coupled to the radiation detector configured to:
receive an indication of the photoluminescence radiation from the radiation detector,
discriminate between the target and a remainder of a treatment site based on the photoluminescence radiation,
determine a distance between the distal end of the fiber and the target based on the photoluminescence radiation, and
provide feedback to a user to indicate the distance.

2. The controller of claim 1, wherein the treatment radiation has a wavelength of about 1600 nm to about 2500 nm.

3. The controller of claim 1, wherein the controller is further configured to control the second laser source to pulse the excitation radiation at a rate between 100 picoseconds and 100 milliseconds.

4. The controller of claim 1, wherein the wavelength of the excitation radiation is about 532 nm.

5. The controller of claim 1, wherein the controller is further configured to control the first laser source to deliver the treatment radiation with a wavelength in the invisible spectrum of light.

6. The controller of claim 1, wherein the controller is further configured to compare an intensity of the photoluminescence radiation to a threshold intensity to discriminate the target from the remainder of the treatment site.

7. The controller of claim 6, wherein the controller is further configured to stop damaging the target via the treatment radiation based on the intensity of the photoluminescence radiation.

8. The controller of claim 6, wherein the controller is further configured to stop damaging the target via the treatment radiation when the intensity of the photoluminescence radiation is above the threshold intensity.

9. The controller of claim 1, wherein the controller is further configured to control the first laser source to damage the target via the treatment radiation in response to the photoluminescence radiation from the treatment site.

10. A controller for a laser system, the controller configured to:
    select an energy of an excitation radiation based on a tissue type of a target to be discriminated;
    send a control signal to an excitation laser source to cause the excitation laser source to generate the excitation radiation in a pulsed manner;
    receive, from a radiation detector, an indication of a photoluminescence radiation emitted by the target responsive to illumination of the target with the excitation radiation, wherein the excitation radiation is delivered to the target via an optical fiber;
    discriminate between the target and a remainder of a treatment site based on the photoluminescence radiation being greater than a threshold;
    determine a distance between a distal end of the optical fiber and the target based on the photoluminescence radiation; and
    send a control signal to an ablation laser source to generate ablation energy.

11. The controller of claim 10, wherein the controller is configured to integrate all wavelengths contained in the photoluminescence radiation into a single intensity value.

12. The controller of claim 10, wherein the controller is further configured to:
    control the ablation laser source to generate the ablation energy in a pulsed manner; and
    control the excitation laser source to generate the excitation radiation having a wavelength in the invisible spectrum of light.

13. The controller of claim 10, wherein the controller is further configured to control the ablation laser source to stop damaging the target via the ablation energy based on the intensity of the received photoluminescence radiation.

14. The controller of claim 10, wherein the controller is further configured to control the ablation laser source to stop damaging the target via the ablation energy when the intensity of the photoluminescence radiation is below a threshold intensity.

* * * * *